US011045469B2

(12) United States Patent
Campbell et al.

(10) Patent No.: US 11,045,469 B2
(45) Date of Patent: Jun. 29, 2021

(54) COMPOSITIONS AND METHODS FOR TREATING INFLAMMATORY BOWEL DISEASE USING A COMBINATION THERAPY OF SMALL MOLECULE INHIBITORS OF C-C CHEMOKINE RECEPTOR TYPE 9 (CCR9) AND ANTI-α4β7 INTEGRIN BLOCKING ANTIBODIES

(71) Applicant: ChemoCentryx, Inc., Mountain View, CA (US)

(72) Inventors: James Campbell, Mountain View, CA (US); Israel Charo, Mountain View, CA (US); Thomas Schall, Mountain View, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

(21) Appl. No.: 15/929,647

(22) Filed: May 14, 2020

(65) Prior Publication Data

US 2020/0268751 A1    Aug. 27, 2020

Related U.S. Application Data

(60) Division of application No. 16/708,167, filed on Dec. 9, 2019, which is a continuation of application No. 14/875,506, filed on Oct. 5, 2015, now Pat. No. 10,532,051.

(60) Provisional application No. 62/060,454, filed on Oct. 6, 2014.

(51) Int. Cl.
| | |
|---|---|
| *A61K 31/502* | (2006.01) |
| *A61K 31/4412* | (2006.01) |
| *A61K 31/4709* | (2006.01) |
| *A61K 31/517* | (2006.01) |
| *A61K 31/415* | (2006.01) |
| *A61K 31/5377* | (2006.01) |
| *A61K 39/395* | (2006.01) |
| *C07K 16/28* | (2006.01) |
| *A61P 1/00* | (2006.01) |

(52) U.S. Cl.
CPC .......... *A61K 31/502* (2013.01); *A61K 31/415* (2013.01); *A61K 31/4412* (2013.01); *A61K 31/4709* (2013.01); *A61K 31/517* (2013.01); *A61K 31/5377* (2013.01); *A61K 39/395* (2013.01); *A61P 1/00* (2018.01); *C07K 16/2842* (2013.01)

(58) Field of Classification Search
CPC ............... A61K 31/502; A61K 31/415; A61K 31/4412; A61K 31/4709; A61K 31/517; A61K 31/5377; A61K 39/395; A61P 1/00; C07K 16/2842
See application file for complete search history.

(56) References Cited

U.S. PATENT DOCUMENTS

| | | | |
|---|---|---|---|
| 6,939,885 B2 * | 9/2005 | Ungashe | A61P 37/00 514/358 |
| 7,238,717 B2 | 7/2007 | Fleming et al. | |
| 7,420,055 B2 | 9/2008 | Ungashe et al. | |
| 7,582,661 B2 | 9/2009 | Ugashe et al. | |
| 7,683,176 B2 | 3/2010 | Charvat et al. | |
| 7,718,683 B2 | 5/2010 | Charvat et al. | |
| 7,776,877 B2 | 8/2010 | Charvat et al. | |
| 7,932,252 B2 | 4/2011 | Ungashe et al. | |
| 8,198,414 B2 | 6/2012 | Cruwys et al. | |
| 8,211,896 B2 | 7/2012 | Ungashe et al. | |
| 8,916,601 B2 | 12/2014 | Chen et al. | |
| 9,133,124 B2 | 9/2015 | Pennell et al. | |
| 9,139,526 B2 | 9/2015 | Bis et al. | |
| 9,150,513 B2 | 10/2015 | Bis et al. | |
| 2009/0005410 A1 | 1/2009 | Charvat et al. | |
| 2010/0075963 A1 | 3/2010 | Lehr et al. | |
| 2010/0331302 A1 | 12/2010 | Charvat et al. | |
| 2011/0130426 A1 | 6/2011 | Bladh et al. | |
| 2012/0282249 A1 | 11/2012 | Fox et al. | |
| 2012/0283411 A9 | 11/2012 | Currie et al. | |
| 2012/0301462 A1 | 11/2012 | Cruwys et al. | |
| 2013/0225580 A1 | 8/2013 | Chen et al. | |

FOREIGN PATENT DOCUMENTS

| | | |
|---|---|---|
| CN | 101855206 A | 10/2010 |
| CN | 103608071 A | 2/2014 |
| RU | 2466139 C2 | 11/2012 |
| WO | 0200651 A2 | 1/2002 |

(Continued)

OTHER PUBLICATIONS

Villablanca et al. (Gastroenterology, 2011, 140, p. 1776-1784).*
American Journal of Gastroenterology, vol. 109, Supplement 2, (Oct. 2014), pp. S523-S524.
Babu, Subash et al., "Chemokine Receptors of T Cells and of B Cells in Lymphatic Filarial Infection: A Role for CCR9 in Pathogenesis," JID (Mar. 15, 2005) 191:1018-1026.
Bekker, Pirow et al., "CCR9 Antagonists in the Treatment of Ulcerative Colitis," Mediators of Inflamation (Accepted Jun. 25, 2015); vol. 2015, Article ID 628340; 10 pages.
Campbell, Daniel J. et al., "Rapid Acquisition of Tissue-specific Homing Phenotypes by CD4 T Cells Activated in Cutaneous or Mucosal Lymphoid Tissues," J. Exp. Med. (Jan. 7, 2002); 195(1):135-141.

(Continued)

*Primary Examiner* — Robert H Havlin
(74) *Attorney, Agent, or Firm* — Barnes & Thornburg LLP; Ryan L. Marshall; Jonathan M. Hartley

(57) ABSTRACT

Provided herein are compositions, methods and kits for treating inflammatory bowel disease (IBD) such as Crohn's disease and ulcerative colitis in a mammal in need thereof. The method include administering to a subject with IBD a combination therapy containing a therapeutically effective amount of a chemokine receptor 9 (CCR9) inhibitor compound and a therapeutically effective amount of an anti-α4β7 integrin antibody such as vedolizumab. Also provided herein is a kit containing the CCR9 inhibitor compound and anti-α4β7 integrin antibody.

18 Claims, 7 Drawing Sheets

(56) References Cited

FOREIGN PATENT DOCUMENTS

| WO | 03099773 | A1 | 12/2003 |
| WO | 04046092 | A2 | 6/2004 |
| WO | 04058736 | A1 | 7/2004 |
| WO | 04108692 | A1 | 12/2004 |
| WO | 05113513 | A2 | 12/2005 |
| WO | 08008374 | A2 | 1/2008 |
| WO | 2008002971 | A2 | 1/2008 |
| WO | 09038847 | A1 | 3/2009 |
| WO | 12064715 | A1 | 5/2012 |
| WO | 12151248 | A2 | 11/2012 |
| WO | 13130811 | A1 | 9/2013 |

OTHER PUBLICATIONS

Database Chemcats; XP-002694860; Accession Nos. 0031290439; 0089984982; 0089999397; 0090861840; 0090892613; 0090315498; 0089721216; 0089950866; 0090856581; 0091040251; Catalog Name: Ambinter Stock Screening Collection; CAS Registry No. 1177125-28-8; (Jan. 1, 2013); 7 pages.
Deepak, M.D., Parakkal et al., "T-Cell Non-Hodgkin's Lymphomas Reported to the FDA AERS With Tumor Necrosis Factor-Alpha (TNF-a) Inhibitors: Results of the REFURBISH Study," Am J Gastroenterol (2013; published online Oct. 2, 2012); 108:99-105.
Diamond, Jonathan R. et al., "Macrophages, monocyte chemoattractant peptide-1, and TGF-1 in experimental hydronephrosis," American Journal of Physiology (Jun. 1994); 266(6):F926-F933 and title page.
Eddy, Allison A. et al., "Renal expression of genes that promote interstitial inflammation and fibrosis in rats with protein-overload proteinuria," Kidney International (accepted for pub Jan. 5, 1995); 47:1546-1557.
Eksteen, Beaus et al., "Hepatic Endothelial CCL25 Mediates the Recruitment of CCR9+ Gut-homing Lymphocytes to the Liver in Primary Sclerosing Cholangitis," J. Exp. Med. (Dec. 6, 2004); 200(11):1511-1517.
Engel, Daniel R. et al., "T helper type 1 memory cells disseminate postoperative ileus over the entire intestinal tract," Nature Medicine (Dec. 2010; pub online Nov. 28, 2010); 16(12):1407-1414.
Extended European Search Report corresponding EP 15848916.1 dated Apr. 13, 2018, 12 pages.
Gonzalez-Cuadrado, S. et al., "Expression of leucocyte chemoattractants by interstitial renal fibroblasts: up-regulation by drugs associate with interstitial fibrosis," Clin Exp Immunol (accepted for pub Jul. 18, 1996); 106:518-522.
International Search Report and Written Opinion corresponding to PCT/US2015/054077 dated Jan. 7, 2016; 11 pages.
International Search Report and Written Opinion corresponding to PCT/US2013/028328 dated Feb. 28, 2013; 14 pages.
Keshav, Salish et al., "A Randomized Controlled Trial of the Efficacy and Safety of CCX282-B, an Orally Adminislered Blocker of Chemokine Receptor CCR9, for Patients with Crohn's Disease," PLOS ONE (Mar. 20, 2013); 8(3):e60094 (12 pages).
Kontoyiannis, Dimilris et al., "Genetic Dissection of the Cellular Pathways and Signaling Mechanisms in Modeled Tumor Necrosis Factor-induced Crohn's-like Inflammatory Bowel Disease," J. Exp. Med. (Dec. 16, 2002); 196 (12):21563-1574.
Kubinyi (3D ASAR in Drug Design: Ligand-Protein Interactions and Molecular Similarity, vol. 2-3, Springer, 1998, 800 pages (pp. 243-244 provided).
Kunkel, Eric J. et al., "Lymphocyte CC Chemokine Receptor 9 and Epithelial Thymus-expressed Chemokine (TECK) Expression Distinguish the Small Intestinal Immune Compartment: Epithelial Expression of Tissue-specific Chemokines as an Organizing Principle in Regional Immunity," J. Exp. Med. (Sep. 4, 2000) 192(5):761-767.
Lloyd, Clare M. et al., "RANTES and Monocyte Chemoattractanl Prolein-1 (MCP-1) Play an Important Role in the Inflammatory Phase of Crescentic Nephritis, but Only MCP-1 is Involved in Crescent Foundation and Interstitial Fibrosis," J. Exp. Med. (Apr. 7, 1997); 185(7)1371-1380.
Morii, Tsukasa et al., "Association of monocyte chemoattractanl prolein-1 with renal tubular damage in diabetic neuropathy," Journal of Diabetes and Its Complications (2003; accepted Mar. 11, 2002); 17:11-15.
Mulder, Daniel J. et al., "A tale of two diseases: The history of inflammatory bowel disease," Journal of Crohn's and Colitis (2014; accepted Sep. 7, 2013); 8:341-348.
Pandya et al., (Bioorg. Med. Chem. Lett. 26 (2016) pp. 3322-3325)).
Papadakis, Konslanlinos A. et al., "CCR9-Positive Lymphocytes and Thymus-Expressed Chemokine Distinguish Small Bowel From Colonic Crohn's Disease," Gastroenterology (Aug. 2001; accepted Jun. 21, 2001); 121:246-254.
Papadakis, Konslanlinos A. et al., "The Role of Thymus-Expressed Chemokine and Its Receptor CCR9 on Lymphocytes in the Regional Specialization of the Mucosal Immune System," The Journal of Immunology (accepted or pub Jul. 31, 2000).
Press Release: "Regeneron's Eylea combination therapy fails mid-stage study," Reuters, by Natalie Grover; Sep. 30, 2016 (2 pages).
Registry STN Tokyo: Registry Copyright 2016 ACS on STN entered Aug. 30, 2009: RN 1177996-59-6; RN 1177981-13-3; RN 1177948-38-7; RN 1177920-00-1; RN 1177898-89-3; RN 1177808-74-0; 1177743-40-6; RN 1177735-96-4; RN 1177679-16-1; RN 1177643-05-8 (5 pages).
Rivera-Nieves, Jesus et al., "Antibody Blockade of CCL25/CCR9 Ameliorates Early but not Late Chronic Murine Ileitis," Gastroenterology (Nov. 2006; online Aug. 31, 2006); 131:15181-1529.
Sales-Campos, H. et al., Classical and recent advances in the treatment of inflammatory bowel diseases; Braz J Mez Biol Res (2015) first published online Nov. 28, 2014); 48(2):96-107.
Schall, Thomas J. et al., Chemokines, leukocyle trafficking, and inflammation; Current Opinion in Immunology (Dec. 1994) 6:865-873.
Schall, Thomas J., "Biology of the Rantes/SIS Cytokine Family," Cytokine (May 1991); 3(3):165-183.
Segerer, Stephan et al., "Chemokines, Chemokine Receptors, and Renal Disease: From Basic Science to Pathophysiologic and Therapeutic Studies," J. Am Soc. Neprol. (2000; Accepted Oct. 2, 1999); 11:152-176.
Uehara, Shoji et al., A Role for CCR9 in T Lymphocyle Development and Migration; The Journal of Immunology (accepted for pub Jan. 18, 2002); 168:2811-2819.
Villablanca, Eduardo J. et al., Blocking Lymphocyle Localization to the Gastrointestinal Mucosa as a Therapeutic Strategy for Inflammatory Bowel Diseases; Gastroenterology (Accepted Feb. 7, 2011) 140(6):1776-1784.
Walters, Matthew J. et al., "CCR9 inhibition does not interfere with the development of immune tolerance to oral antigens," Immune Lett (Accepted Jan. 7, 2013), http://dx.doi.org/10.106/j.imlet.2013. 01.006; 5 pages.
Wermuth, The Practice of Medicinal Chemistry, 2d ed. (2003), 768 pages (chs. 9-10 provided).
Wurbel, Marc-Andre et al., "Mice lacking the CCR9 CC-chemokine receptor show a mild impairment of early T-and B-cell development and a reduction in T-cell receptor gut intraepithelial lymphocytes," Blood (Nov. 1, 2001); 98 (9):2626-2632.
Zaballos, Angel et al., "Cutting Edge: Identification of the Orphan Chemokine Receptor GPR-9-6 as CCR9, the Receptor for the Chemokine TECK1," The Journal of Immunology, (accepted for pub Mar. 16, 1999); 162:5671-5675.
Zabel, Brian A. et al., "Human G Protein-coupled Receptor GPR-9-6/CC Chemokine Receptor 9 is Selectively Expressed on Intestinal Homing T Lymphocytes, Mucosal Lymphocytes, and Thymocytes and is Required for Thymus-expressed Chemokine-mediated Chemotaxis," J. Exp. Med. (Nov. 1, 1999); 190(9):1241-1255.
Walters et al., "Tu1652 CCX507, an Orally Bioavailable Antagonist of the Chemokine Receptor CCR9, for the Treatment of IBD," Gastroenterology, vol. 144, Issue 5, Suppl 1, (2013WO0, p. S815.

* cited by examiner

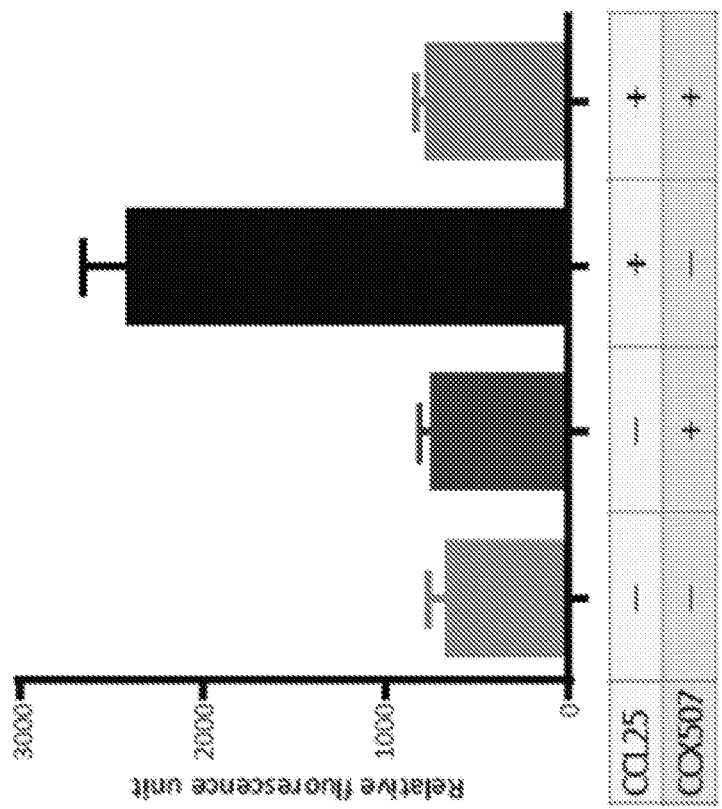
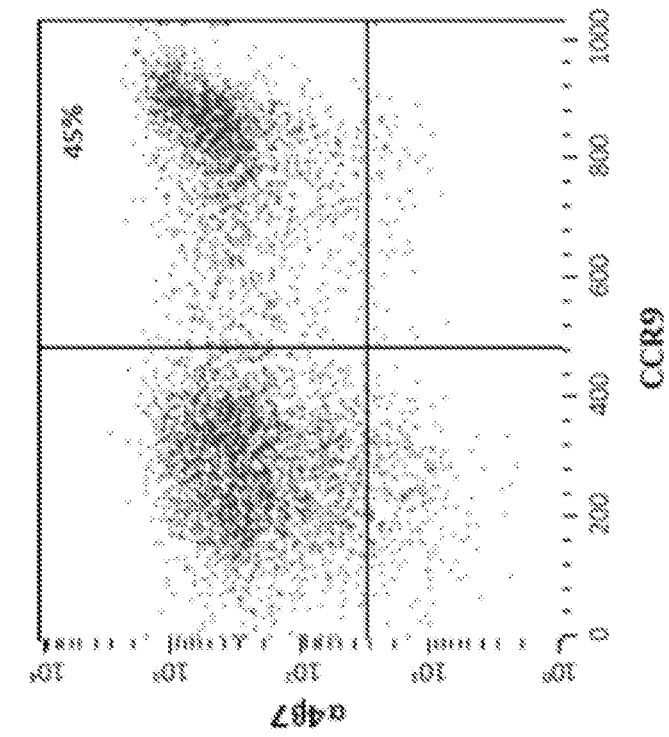
FIG. 1A
FIG. 1B

- ● vehicle
- ▨ rat IgG2a
- △ CCX507 only
- ▽ anti-α4β7 integrin antibody only
- ◆ CCX507 and anti-α4β7 integrin antibody

- □ no treatment
- ● vehicle/rat IgG2A
- ▨ CCX507 only
- ▽ anti-TNFα antibody only
- ○ CCX507 and anti-TNFα antibody

COMPOSITIONS AND METHODS FOR TREATING INFLAMMATORY BOWEL DISEASE USING A COMBINATION THERAPY OF SMALL MOLECULE INHIBITORS OF C-C CHEMOKINE RECEPTOR TYPE 9 (CCR9) AND ANTI-α4β7 INTEGRIN BLOCKING ANTIBODIES

CROSS-REFERENCES TO RELATED APPLICATIONS

This application is a divisional application of U.S. patent application Ser. No. 16/708,167, filed Dec. 9, 2019, which is a continuation application of U.S. patent application Ser. No. 14/875,506, filed Oct. 5, 2015, which claims priority to U.S. Provisional Application No. 62/060,454, filed Oct. 6, 2014, the disclosures of which are hereby incorporated by reference in their entirety for all purposes.

BACKGROUND OF THE INVENTION

Inflammatory bowel disease (IBD) is a group of chronic inflammatory conditions that affects part or all of the gastrointestinal (GI) tract such as the mouth, esophagus, stomach, small intestines, large intestines (colon), rectum, and anus. IBD includes Crohn's disease (CD), ulcerative colitis (UC), and indeterminate colitis. CD and UC can be distinguished by clinical, endoscopic and pathological features.

CD is a disease of chronic inflammation that can involve any part of the GI tract. Characteristic symptoms of the disease include severe abdominal pain, frequent diarrhea, rectal bleeding, rectal urgency, and swelling of the lower right abdomen.

UC is a chronic intermittent remitting inflammatory disease of the colon. The disease is characterized by recurring episodes of inflammation primarily involving superficial mucosal lesions that extend through the rectum and upwards through the colon. Acute episodes are characterized by chronic diarrhea or constipation, rectal bleeding, cramping and abdominal pain.

IBD is characterized by inflammation and the infiltration of leukocytes such as lymphocytes, granulocytes, monocytes and macrophages from the blood to the mucosal or epithelial lining of the intestines. Multiple inflammatory cell types including lymphocytes, neutrophils, macrophages and dendritic cells contribute to IBD. T lymphocytes, for instance, infiltrate the mucosa of the gastrointestinal tract through coordinated interactions between adhesion molecules on the surface of the T lymphocyte and their cognate ligand on the endothelium. For example, α4β7 integrin which expressed on the surface of some T and B lymphocytes directs the migration of these cells by binding to one of its ligands, mucosal addressin cell adhesion molecule 1 (MAdCAM-1) on endothelial cells of the GI tract. Chemokine receptors and ligands, e.g., the receptor CCR9 and its ligand CCL25 also play a role in the migration of inflammatory cells, e.g., effector memory T helper cells into the intestine epithelium in IBD.

Current therapies for treating IBD include surgery or use of anti-tumor necrosis factor (anti-TNFα) antibodies, e.g., infliximab and adalimumab, aminosalicylates, systemic corticosteroids, immunosuppressants, e.g., thiopurines and methotrexate, and combinations thereof. Unfortunately, some patients with IBD do not respond to or cannot tolerate such drug treatments.

In view of the above, it is apparent that effective treatment regimens for IBD that are able to block multiple pathways and/or multiple cell types associated with lymphocyte infiltration can be useful for treating the disease. The present invention provides such therapies along with pharmaceutical compositions and related methods of treatment.

BRIEF SUMMARY OF THE INVENTION

In one aspect, the present disclosure provides a method of treating or reducing the development of inflammatory bowel disease in a mammal, said method comprising administering a suitable amount of a CCR9 chemokine receptor inhibitor with an anti-α4β7 integrin blocking antibody. In some embodiments, the inflammatory bowel disease is Crohn's disease (CD) or ulcerative colitis (UC).

In some embodiments, the CCR9 chemokine receptor inhibitor is a small molecule receptor inhibitor having a molecular weight of less than 1500. The CCR9 small molecule receptor inhibitor can have a molecular weight of about 1495, 1450, 1400, 1300, 1200, 1100, 1000, 900, 800, 700, 600, 500, or less.

In other embodiments, the CCR9 chemokine receptor inhibitor is a small molecule receptor inhibitor having a molecular weight of less than 750. The CCR9 small molecule receptor inhibitor can have a molecular weight of about 745, 700, 650, 600, 550, 500, 450, 400, 350, 300 or less.

In some embodiments, the CCR9 small molecule inhibitors provided herein may be represented by formula (I) or salts thereof:

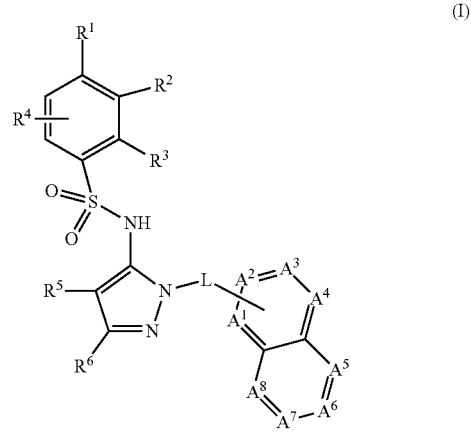

(I)

where $R^1$, $R^2$, $R^3$, $R^4$, $R^5$, $R^6$, L, $A^1$, $A^2$, $A^3$, $A^4$, $A^5$, $A^6$, $A^7$, and $A^8$ are as defined below.

In some embodiments, the anti-α4β7 integrin blocking antibody is vedolizumab (ENYVIO®), or a biosimilar, biobetter, or bioequivalent thereof. In other embodiments, the anti-α4β7 integrin blocking antibody is vedolizumab (ENYVIO®).

In some embodiments, the CCR9 chemokine receptor inhibitor and the anti-α4β7 integrin blocking antibody are administered in a combination formulation. In other embodiments, the CCR9 chemokine receptor inhibitor and the anti-α4β7 integrin blocking antibody are administered sequentially. In yet other embodiments, the CCR9 chemokine receptor inhibitor is administered prior to the anti-α4β7 integrin blocking antibody. In another embodiment, the CCR9 chemokine receptor inhibitor is administered after administration of the anti-α4β7 integrin blocking antibody.

In some embodiments, the CCR9 chemokine receptor inhibitor is a compound having the formula:

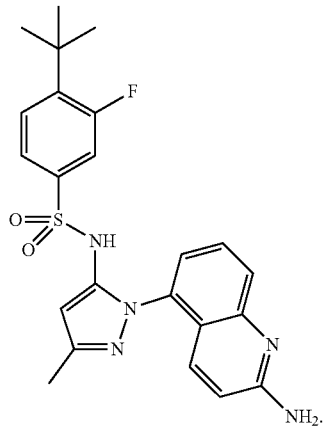 [SMILES: Cc1cc(NS(=O)(=O)c2ccc(C(C)(C)C)c(F)c2)n(-c2cccc3nc(N)ccc23)n1]

In another aspect, the present disclosure provides a composition for treating or reducing the development of inflammatory bowel disease in a mammal, said composition comprising a therapeutically effective amount of a CCR9 chemokine receptor inhibitor, a therapeutically effective amount of an anti-α4β7 integrin blocking antibody, and a pharmaceutically acceptable carrier or excipient.

In some embodiments, the inflammatory bowel disease is Crohn's disease (CD) or ulcerative colitis (UC).

In some embodiments, the CCR9 chemokine receptor inhibitor is a small molecule receptor inhibitor having a molecular weight of less than 1500. In other embodiments, the CCR9 chemokine receptor inhibitor is a small molecule receptor inhibitor having a molecular weight of less than 750. The CCR9 chemokine receptor inhibitor compound may be represented by formula (I) or salt thereof, as described herein.

In some embodiments, the anti-α4β7 integrin blocking antibody is vedolizumab (ENYVIO®), or a biosimilar, biobetter, or bioequivalent thereof. In other embodiments, the anti-α4β7 integrin blocking antibody is vedolizumab (ENYVIO®).

In yet another aspect, the present disclosure provides a kit for treating or reducing the development of inflammatory bowel disease in a mammal, said kit comprising a therapeutically effective amount of a CCR9 chemokine receptor inhibitor, a therapeutically effective amount of an anti-α4β7 integrin blocking antibody, and instructions for effective administration.

In some embodiments, the CCR9 chemokine receptor inhibitor and the anti-α4β7 integrin blocking antibody are formulated for sequential administration. In other embodiments, the CCR9 chemokine receptor inhibitor and the anti-α4β7 integrin blocking antibody are formulated for concomitant administration.

In some embodiments, the CCR9 chemokine receptor inhibitor is a small molecule receptor inhibitor having a molecular weight of less than 1500. In other embodiments, the CCR9 chemokine receptor inhibitor is a small molecule receptor inhibitor having a molecular weight of less than 750. The CCR9 chemokine receptor inhibitor compound may be represented by formula (I) or salt thereof, as described herein. In some instances, the small molecule receptor inhibitor is vercirnon (Traficet-EN™) or CCX507.

In some embodiments, the anti-α4β7 integrin blocking antibody is vedolizumab (ENYVIO®)), or a biosimilar, biobetter, or bioequivalent thereof. In other embodiments, the anti-α4β7 integrin blocking antibody is vedolizumab (ENYVIO®).

Other objects, features, and advantages of the present invention will be apparent to one of skill in the art from the following detailed description and figures.

BRIEF DESCRIPTION OF THE DRAWINGS

FIGS. 1A and 1B shows that a small molecule inhibitor of CCR9 (CCX507) limits the binding of retinoic acid differentiated human T cells to MAdCAM-1. FIG. 1A shows human PBMCs were activated with CD3ε and CD28 in the presence of retinoic acid and IL-12. Expression of gut-tropic factors, CCR9 and α4β7, are depicted as a two parameter dot plot. The percentage of CCR9$^+$ α4β7$^+$ cells is shown. FIG. 1B shows data of a static binding assay of in vitro differentiated human CCR9$^+$ 4β7$^+$ cells. Briefly, CCR9$^+$ α4β7$^+$ cells were mixed with 500 nM of hCCL25 in the presence or absence of 1 μM CCX507 and added to MAdCAM-1-Fc coated plates. The number of cells adhering to MAdCAM-1 under each condition was quantified using CyQUANT® and depicted as relative fluorescence unit (RFU).

FIG. 2A shows the experimental design used to determine the in vivo pharmacodynamic range of CCX507 in a short-term T cell trafficking model. The number of OT-I derived CD8$^+$ intra-epithelial lymphocytes (IELs) in the presence of 5-30 mg/kg of CCX507 is shown in FIG. 2B and in the presence of an anti-α4β7 integrin blocking antibody is shown in FIG. 2C, as bar graphs.

FIG. 3 depicts a heat map representing the expression levels of selected genes compared to the expression level of CCR9.

FIG. 4A shows the dosing regimens for anti-α4β7 integrin blocking antibodies and anti-TNFα antibodies. FIG. 4B provides representative photos depicting the colon of wild-type mice (FVB) and mice receiving vehicle control (1% HPMC), rat IgG2a isotype control, CCX507, anti-α4β7 integrin blocking antibody, and a combination of CCX507 and anti-α4β7 integrin blocking antibody. Quantitative colon vs. weight ratios for CCX507/anti-α4β7 integrin blocking antibody (FIG. 4C) and CCX507/anti-TNFα blocking antibody (FIG. 4D) are shown as scatterplots.

FIG. 5A shows representative images of both the proximal and distal colon from individual mice, representative of the mean histopathological score for each group. The combination of CCX507 in addition to anti-α4β7 antibody is shown in the right panel. FIG. 5B provides the sum histological score for all mice in the study.

DETAILED DESCRIPTION OF THE INVENTION

I. Introduction

Figure 2A:
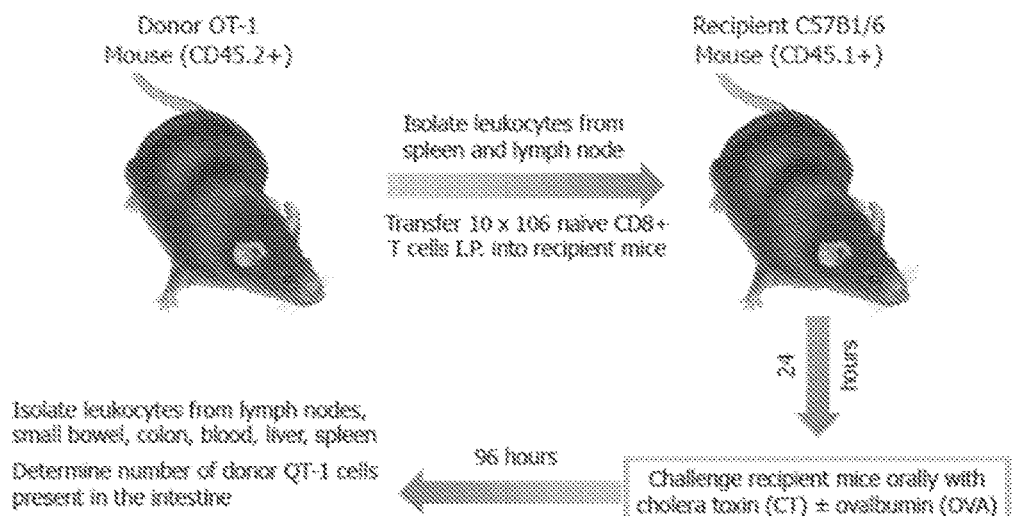
FIGS. 2A, 2B and 2C illustrate in vivo pharmacodynamic efficacy of CCX507 in a mouse model of an adoptive T cell transfer.

The present disclosure is based, in part, on the unexpected discovery that a combination therapy of a CCR9 inhibitor, e.g., a small molecule inhibitor of CCR9, and an antibody against α4β7 integrin can act synergistically in the treatment of inflammatory bowel disease such as Crohn's disease, ulcerative colitis, and indeterminate colitis. Provided herein are methods, compositions and kits for treating IBD in a subject, e.g., human or animal subject, in need thereof. In some embodiments, the method includes administering therapeutically effective amounts of CCX507 (vercirnon) and vedolizumab to a subject with IBD to elicit a clinical response or maintain clinical remission in the subject.

II. Definitions

When describing the compounds, compositions, methods and processes of this invention, the following terms have the following meanings, unless otherwise indicated.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "inflammatory bowel disease" or "IBD" includes gastrointestinal disorders such as, e.g., Crohn's disease (CD), ulcerative colitis (UC), indeterminate colitis (IC), and IBD that is inconclusive for CD vs. UC ("Inconclusive"). Inflammatory bowel diseases (e.g., CD, UC, IC, and Inconclusive) are distinguished from all other disorders, syndromes, and abnormalities of the gastroenterological tract, including irritable bowel syndrome (IBS). Examples of IBD-related diseases include collagenous colitis and lymphocytic colitis.

The term "ulcerative colitis" or "UC" refers to a chronic intermittent and relapsing inflammatory bowel disease (IBD) of the colon or large bowel characterized by superficial mucosal lesions that extend through the rectum and progress upstream. The different types of ulcerative colitis are classified according to the location and extent of inflammation. Examples of UC include, but are not limited to, ulcerative proctitis, proctosigmoiditis, left-sided colitis, and pan-ulcerative (total) colitis.

The term "Crohn's Disease" or "CD" refers to a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and mouth. Examples of UC include, but are not limited to, ileocolitis, ileitis, gastroduodenal Crohn's disease, jejunoileitis, and Crohn's (granulomatous) colitis.

The term "subject," "individual" or "patient" refers to an animal such as a mammal, including, but not limited to, primates (e.g., humans), cows, sheep, goats, horses, dogs, cats, rabbits, rats, mice and the like.

The term "C—C chemokine receptor type 9," "CCR9" or "CCR9 chemokine receptor" refers to a receptor for the chemokine CCL25 which is also known as TECK and SCYA25. The human CCR9 polypeptide sequence is set forth in, e.g., GenBank Accession Nos. NP_001243298, NP_006632, NP_112477, and XP_011531614. The human CCR9 mRNA (coding) sequence is set forth in, e.g., GenBank Accession Nos. NM_001256369, NM_006641, NM_031200, and XM_011533312.

The term "C—C chemokine receptor 9 inhibitor," "CCR9 inhibitor" or "CCR9 chemokine receptor inhibitor" refers to an inhibitor or antagonist of a CCR9 receptor polypeptide, variants thereof, or fragments thereof.

The term "small molecule inhibitor" refers to a small molecule or low molecular weight organic compound that inactivates, inhibits, or antagonizes a target molecule, biomolecule, protein or other biological product.

The term "α4β7 integrin" refers to an heterodimeric integrin molecule that contains two distinct chains such as an α4 chain and a β7 chain. The human integrin alpha 4 chain polypeptide sequence is set forth in, e.g., GenBank Accession No. NP_000876. The human integrin alpha 4 chain mRNA (coding) sequence is set forth in, e.g., GenBank Accession No. NM_000885. The human integrin beta 7 chain polypeptide sequence is set forth in, e.g., GenBank Accession Nos. NP_000880, XP_005268908, and XP_005268909. The human integrin beta 7 chain mRNA (coding) sequence is set forth in, e.g., GenBank Accession Nos. NM_000889, XM_05268851 and XM_05268852. It is also referred to as LPAM.

The term "anti-α4β7 integrin blocking antibody" or "anti-α4β7 integrin neutralizing antibody" refers to an antibody or a fragment thereof that specifically binds to a α4β7 integrin (the α4β7 integrin heterodimer) polypeptide or a fragment thereof. In some cases, an anti-integrin α4β7 blocking antibody blocks the interaction of α4β7 integrin with any one of its ligands.

The term "biosimilar" refers to a biological product that is highly similar to an FDA-approved biological product (reference product) and has no clinically meaningful differences in terms of pharmacokinetics, safety and efficacy from the reference product.

The term "bioequivalent" refers to a biological product that is pharmaceutically equivalent and has a similar bioavailability to an FDA-approved biological product (reference product). For example, according to the FDA the term bioequivalence is defined as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study" (United States Food and Drug Administration, "Guidance for Industry:Bioavailability and Bioequicalence Studies for Orally Administered Drug Products—General Considerations," 2003, Center for Drug Evaluation and Research).

The term "biobetter" refers a biological product that is in the same class as an FDA-approved biological product (reference product) but is not identical and is improved in terms of safety, efficacy, stability, etc. over the reference product.

The term "therapeutically effective amount" refers to that amount of the therapeutic agent sufficient to ameliorate the targeted condition or symptoms. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "administering" or "administration" and derivatives thereof refers to the methods that may be used to enable delivery of agents or compositions to the desired site of biological action. These methods include, but are not limited to parenteral administration (e.g., intravenous, subcutaneous, intraperitoneal, intramuscular, intravascular, intrathecal, intranasal, intravitreal, infusion and local injection), transmucosal injection, oral administration, administration as a suppository, and topical administration. One skilled in the art will know of additional methods for administering a therapeutically effective amount of a compound of the present invention for preventing or relieving one or more symptoms associated with a disease.

The term "treating" or "treatment" refers to the treating or treatment of a disease or medical condition (such as inflammation) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient. The term encompasses the prophylactic treatment of a disease as to prevent or reduce the risk of acquiring or developing a specific disease, or to prevent or reduce the risk of disease recurrence.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). The term "cycloalkyl" by itself or as a part of another substituent refers to a cyclic alkyl group having the number of carbons designated and is a subset of the term "alkyl." Other subsets of the term "alkyl" include "linear" and "branched" alkyl groups which refer to two different types of acyclic alkyl groups. Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. In this list of examples, the methyl, ethyl, n-propyl, and n-butyl alkyl examples are also examples of "linear alkyl" groups. Similarly, isopropyl and t-butyl are also examples of "branched alkyl" groups. Cyclopentyl, cyclohexyl, (cyclohexyl)methyl, cyclopropylmethyl, bicyclo[2.2.1]heptane, bicyclo[2.2.2]octane are examples of "cycloalkyl" groups. In some embodiments, cyclopropyl may be used as a bridging group between two other moieties and represented as —CH(CH$_2$)CH—. "Alkyl groups can be substituted or unsubstituted, unless otherwise indicated. Examples of substituted alkyl include haloalkyl, thioalkyl, aminoalkyl, and the like. Additional examples of suitable substituted alkyl include, but are not limited to, hydroxyisopropyl, —C(CH$_3$)$_2$—OH, aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl. Suitable substituents for substituted alkyl, include halogen, —CN, —CO$_2$R', —C(O)R', —C(O)NR'R", oxo (=O or —O$^-$), —OR', —OC(O)R', —OC(O)NR'R"—NO2, —NR'C(O)R", —NR'''C(O)NR'R", —NR'R", —NR'CO$_2$R", —NR'S(O)R", —NR'S(O)$_2$R''', —NR'''S(O) NR'R", —NR'''S(O)$_2$NR'R", —SR', —S(O)R', —S(O)$_2$R', —S(O)2NR'R", —NR'—C(NHR")=NR''', —SiR'R"R''', —OSiR'R"R''', —N$_3$, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical. With respect to substituted alkyl, R', R" and R''' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6-, or 7-membered ring.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Alkylamino" refers to —N(alkyl)$_2$ or —NH(alkyl). When the alkylamino group contains two alkyl groups, the alkyl groups may be combined together to form a carbocyclic or heterocylic ring. It is to be understood that the alkyl groups of the alkylamino group may be substituted or unsubstituted. Examples of an alkylamino group include methylamino, tert-butylamino, dimethylamino, di-isopropylamino, morpholino, and the like.

"Aminoalkyl", as a substituted alkyl group, refers to a monoaminoalkyl or polyaminoalkyl group, most typically substituted with from 1-2 amino groups. Examples include aminomethyl, 2-aminoethyl, 2-diethylaminoethyl, and the like.

"Aryl" refers to a polyunsaturated, aromatic hydrocarbon group having a single ring (bicyclic) or multiple rings (preferably bicyclic) which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated. Substituted aryl may be substituted with one or more substituents. Suitable substituents for aryl include substituted or unsubstituted $C_{1-8}$ alkyl and those substituents as discussed above for substituted alkyl "Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

Exemplary heterocyclic groups may be represented by formula (AA) below:

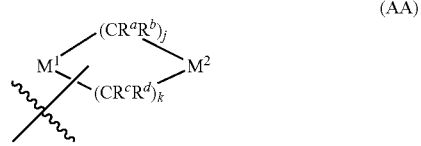

(AA)

where formula (AA) is attached via a free valence on either $M^1$ or $M^2$; $M^1$ represents O, $NR^e$, or $S(O)^l$; $M^2$ represents $CR^fR^g$, O, $S(O)^l$, or $NR^e$; where it may be necessary to omit one $R^f$, $R^g$, or $R^e$ to create a free valence on $M^1$ or $M^2$ such as, for example $CR^f$, $CR^g$, or N; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^h$, —$CO_2R^h$, —$CONR^hR^i$, —$NR^hCOR^i$, —$SO_2R^h$—$SO_2NR^hR^i$, —$NR^hSO_2R^i$—$NR^hR^i$, —$OR^h$, —$SiR^hR^iR^j$, —$OSiR^hR^iR^j$, -$Q^1COR^h$, -$Q^1CO2R^h$, -$Q^1CONR^hR^i$, -$Q^1NR^hCOR^i$, -$Q^1SO_2R^h$, -$Q^1SO_2NR^hR^i$, -$Q^1NR^hSO_2R^i$, -$Q^1NR^hR^i$, -$Q^1OR^h$, wherein $Q^1$ is a member selected from the group consisting of $C_{1-4}$ alkylene, $C_{2-4}$ alkenylene and $C_{2-4}$ alkynylene, and $R^h$, $R^i$ and $R^j$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$, $R^i$ and R substituents are optionally substituted with from one to three members selected from the group consisting of halogen, —OH, —$OR''$, —$OC(O)NHR''$, —$OC(O)NR''R^o$, —SH, —$SR''$, —$S(O)R''$, —$S(O)_2R''$—$S(O)_2NHR''$, —$S(O)_2NR''R^o$, —$NHS(O)_2R''$, —$NR''S(O)_2R^o$, —$C(O)NH_2$, —$C(O)NHR''$, —$C(O)NR''R^o$, —$C(O)R''$, —$NHC(O)R^o$, —$NR''C(O)R^o$, —$NHC(O)NH_2$, —$NR''C(O)NH_2$, —$NR''C(O)NHR^o$, —$NHC(O)NHR''$, —$NR''C(O)NR''R^o$, —$NHC(O)NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, where $R''$, $R^o$ and $R^p$ are independently an unsubstituted $C_{1-8}$ alkyl. Additionally, any two of $R^a$, $R^b$, $R^c$, $R^d$, $R^e$, $R^f$, and $R^g$ be combined to form a bridged or spirocyclic ring system.

Preferably, the number of $R^a+R^b+R^c+R^d$, groups that are other than hydrogen is 0, 1 or 2. More preferably, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —$C(O)R^h$, —$CO_2R^h$, —$C(O)NR^hR^h$, —$NR^hCOR^i$, —$SO_2R^h$, —$SO_2NR^hR^i$, —$NSO_2R^hR^i$, —$NR^hR^i$, and —$OR^h$, where $R^h$ and $R^i$ are independently selected from the group consisting of hydrogen and unsubstituted $C_{1-8}$ alkyl; and where the aliphatic portions of each of the $R^a$, $R^b$, $R^c$, $R^d$, $R^e$, $R^f$, and $R^g$ substituents are optionally substituted with from one to three members selected from the group consisting of halogen, —OH, —$OR''$, —$OC(O)NHR''$, —$OC(O)NR''R^o$, —SH, —$SR''$, —$S(O)R^o$, —$SO_2R''$, —$SO_2NH_2$, —$SO_2NHR''$, —$SO_2NR''OR^o$, —$NHSO_2R''$, —$NR''SO_2R^o$, —$C(O)NH_2$, —$C(O)NHR''$, —$C(O)NR''R^o$, —$C(O)R''$, —$NHC(O)R''$, —$NR''C(O)R^o$, —$NHC(O)NH_2$, —$NR''C(O)NH_2$, —$NR''C(O)NHR^o$, —$NHC(O)NHR''$, —$NR''C(O)NR''R^o$, —$NHC(O)NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, where $R''$, $R^o$ and $R^p$ are independently an unsubstituted $C_{1-8}$ alkyl.

More preferably, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or $O^-$), the resulting group may have either a carbonyl (—C(O)—) or a N-oxide (—$N^+$—$O^-$) or —S(O)— or —$S(O)_2$—.

Suitable substituents for substituted alkyl, substituted alkenyl, and substituted alkynyl include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)$_2$R''', —SR', —S(O)R', —S(O)$_2$R', —S(O)$_2$NR'R", —SiR'R"R''', —N$_3$, substituted or unsubstituted C$_{6-10}$ aryl, substituted or unsubstituted 5- to 10-membered heteroaryl, and substituted or unsubstituted 3- to 10-membered heterocyclyl, in a number ranging from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", —NR'—C(NHR")=NR''', —SiR'R"R''', —N$_3$, substituted or unsubstituted C1-8 alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6-, or 7-membered ring.

Two of the substituents on adjacent atoms of an aryl or heteroaryl ring may optionally be replaced with a substituent of the formula -T-C(O)—(CH$_2$)$_q$—U—, where T and U are independently —NR''''—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, where A' and B' are independently —CH$_2$—, —O—, —NR''''—, —S—, —S(O)—, —S(O)$_2$—, —S(O)$_2$NR''''— or a single bond, and r is an integer from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR''''—, —S—, —S(O)—, —S(O)$_2$—, or —S(O)$_2$NR'—. The substituent R'''' in —NR''''— and —S(O)$_2$NR''''— is hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", *J. Pharmaceutical Science,* 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs may be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The compounds of the invention may be present in the form of pharmaceutically acceptable metabolites thereof. The term "metabolite" refers to a pharmaceutically acceptable form of a metabolic derivative of a compound of the invention (or a salt thereof). In some aspects, the metabolite may be a functional derivative of a compound that is readily convertible in vivo into an active compound. In other aspects, the metabolite may be an active compound.

The term "acid isosteres" refers to, unless otherwise stated, a group which can replace a carboxylic acid, having an acidic functionality and steric and electronic characteristics that provide a level of activity (or other compound characteristic such as solubility) similar to a carboxylic acid. Representative acid isosteres include: hydroxamic acids, sulfonic acids, sulfinic acids, sulfonamides, acyl-sulfonamides, phosphonic acids, phosphinic acids, phosphoric acids, tetrazole, and oxo-oxadiazoles.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 I ($^{125}$I) or carbon-14 ($^{14}$C). All isotopic variations of the compounds of the present invention, whether radioactive or not, are intended to be encompassed within the scope of the present invention.

The compounds of the present invention may include a detectable label. A detectable label is a group that is detectable at low concentrations, usually less than micromolar, probably less than nanomolar and possibly less than picomolar, and that can be readily distinguished from other molecules, due to differences in a molecular property (e.g. molecular weight, mass to charge ratio, radioactivity, redox potential, luminescence, fluorescence, electromagnetic properties, binding properties, and the like). Detectable labels may be detected by spectroscopic, photochemical, biochemical, immunochemical, electrical, magnetic, electromagnetic, optical or chemical means and the like.

A wide variety of detectable labels are within the scope of the present invention, including hapten labels (e.g., biotin, or labels used in conjunction with detectable antibodies such as horse radish peroxidase antibodies); mass tag labels (e.g., stable isotope labels); radioisotopic labels (including $^3$H, $^{125}$I, $^{35}$S, $^{14}$C, or $^{32}$P); metal chelate labels; luminescent labels including fluorescent labels (such as fluorescein, isothiocyanate, Texas red, rhodamine, green fluorescent protein, and the like), phosphorescent labels, and chemiluminescent labels, typically having quantum yield greater than 0.1; electroactive and electron transfer labels; enzyme modulator labels including coenzymes, organometallic catalysts horse radish peroxidase, alkaline phosphatase and others commonly used in an ELISA; photosensitizer labels; magnetic bead labels including Dynabeads; colorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; and carbon black labels. Patents teaching the use of such detectable labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

Detectable labels are commercially available or may be prepared as known to one skilled in the art. Detectable labels may be covalently attached to the compounds using a reactive functional group, which can be located at any appropriate position. Methods for attaching a detectable label are known to one skilled in the art. When the reactive group is attached to an alkyl, or substituted alkyl chain tethered to an aryl nucleus, the reactive group may be located at a terminal position of an alkyl chain.

III. Detailed Descriptions of Embodiments

A. Treating Inflammatory Bowel Disease with a Combination Therapy

The present disclosure provides methods, compositions and kits based on a combination therapy that includes a CCR9 inhibitor and an anti-α4β7 integrin antibody. This therapy is useful for treating IBD such as Crohn's disease (CD) and ulcerative colitis (UC) in a subject. The present invention is based, in part, on the unexpected discovery that the synergistic combination of a CCR9 inhibitor and an anti-α4β7 integrin antibody is effective at treating IBD.

1. Crohn's Disease

The compositions, methods and kits of the present invention can be used to a subject with CD, including all types of CD. The combination therapy of a CCR9 inhibitor and an anti-α4β7 integrin antibody can be administered at an effective amount to induce a clinical response or maintain clinical remission in a subject with CD. In some embodiments, the combination therapy mitigates, reduces or minimizes the severity of one or more symptoms of CD.

Symptoms of CD include diarrhea, fever, fatigue, abdominal pain or cramping, blood in stool, mouth sores, reduced appetite, weight loss, and perianal disease. Additional symptoms or characteristics of CD can be evaluated by endoscopy, e.g., esophagogastroduodenoscopy, colonoscopy, sigmoidoscopy, endoscopic retrograde cholangiopancreatography, endoscopic ultrasound, and balloon endoscopy, and histology of biopsies form the GI tract. The severity of the disease can be categorized as mild to moderate, moderate to severe, and severe/fulminant disease. Additional descriptions about CD found in, for example, Lichtenstein et al., *Am J Gastroenterol*, 2009, 104(2):2465-83.

Severity of CD as well as clinical response to combination therapy can be determined using a clinical index such as the Crohn's Disease Activity Index or CDAI (Best et al., *Gastroenterology*, 1976, 70:439-44). The index is used to quantify the symptoms of patients with CD. The CDAI can be used to define clinical response or remission of CD. The CDAI consists of eight factors, each added together (summed) after adjustment with a weighting factor or multiplier. The eight factors include number of liquid stools, abdominal pain, general well-being, extraintestinal complications, antidiarrheal drugs, abdominal mass, hemacrit, and body weight. Remission of Crohn's disease is generally defined as a fall or decrease in the CDAI of less than 150 points. Severe disease is typically defined as a value of greater than 450 points. In certain aspects, response to a particular medication in a Crohn's disease patient is defined as a fall of the CDAI of greater than 70 points from baseline (week 0 of treatment).

Clinical index such as the CDAI can be used to determine whether the combination therapy described herein induces a clinical response or clinical remission in a patient with Crohn's disease. In some embodiments, if the patient's CDAI score decreases by 70 point or more from baseline upon receiving the combination therapy, the patient is having a clinical response. If the patient's CDAI score decreases to less than 150 points at the end of the induction phase of therapy, the patient is in clinical remission of CD.

2. Ulcerative Colitis

The compositions, methods and kits of the present invention can be used to a subject with UC, including all types of UC. The combination therapy of a CCR9 inhibitor and an anti-α4β7 integrin antibody can be administered at an effective amount to induce a clinical response or maintain clinical remission in a subject with UC. In some embodiments, the combination therapy mitigates, reduces or minimizes the severity of one or more symptoms of UC.

Symptoms of UC include, but are not limited to, diarrhea, abdominal pain and cramping, rectal pain, rectal bleeding, urgency to have a bowel movement, inability to have a bowel movement, weight loss, fatigue, fever, or anemia. The severity of the disease can be categorized as mild to moderate, moderate to severe, and severe/fulminant disease. See, e.g., Kornbluth et al., *Am J Gastroenterol*, 2004, 99(7):1371-85.

Disease activity of UC and response to treatment can be assessed by quantitative analysis using a composite index scoring system. Generally, clinicians consider at least four factors or variables when assessing UC disease activity: clinical symptoms, quality of life, endoscopy evaluation, and histology assessment. For example, the colitis activity index (CAI) is a quantitative measurement of incorporates the following disease symptoms: inflammation in the colon based on colonoscopy, diarrhea, abdominal pain and cramping, and blood stool. Standardized endoscopic score systems such as the UC Endoscopic Index of Severity (UCEIS) are useful for establishing a patient's disease index score. Other useful disease activity indices include the Mayo Clinic Score (see, e.g., Rutgeert et al., N Eng J Med, 2005, 353(23):2462-76) and the modified Mayo Disease Activity Index (MMDAI; see, e.g., Schroeder et al., N Eng J Med, 1987, 317(26):1625-9). The four factors used in the Mayo Clinic scoring system include stool (bowel) frequency, rectal bleeding, endoscopic findings, and the physician's global assessment of disease severity (e.g., daily abdominal discomfort and general sense of well-being).

Compared to the Mayo Clinic Score, MMDAI includes the removal of "friability" from the endoscopy score of 1. Therefore, the presence of friability reflects an endoscopy score of 2 or 3. The MMDAI evaluates 4 subscores (bowel frequency, rectal bleeding, endoscopic appearance, and physician's global assessment), each on a scale of 0 to 3 with a maximum total score of 12.

In some embodiments, clinical response by a subject with UC to a combination therapy provided herein corresponds to a decrease of 2 points or greater from baseline in the MMDAI score and a 25% or greater decrease from baseline, and/or a decrease of a 1 point or greater from baseline in the rectal bleeding subscore. In other embodiments, clinical response corresponds to a decrease of 3 points or greater in Mayo Clinic Score and 30% from baseline Clinical remission by a UC subject administered the combination therapy can correspond to a score of 0 for rectal bleeding and a combined score of 2 point or lower for bowel frequency and physician's assessment using the MMDAI subscale. In other embodiments, clinical remission in a subject with UC refers to having a Mayo Clinic Score of 2 point or less and no individual subscore (bowel frequency, rectal bleeding, endoscopic appearance, and physician's global assessment) of more than 1 point.

B. Combination Therapy of CCR9 Inhibitors and Anti-α4β7 Integrin Antibodies

Provided herein are methods, compositions and kits that take advantage of the synergistic effect of CCR9 inhibitors and anti-α4β7 integrin antibodies in reducing inflammation in subjects with IBD. A combination treatment that includes both a CCR9 inhibitor and an anti-α4β7 integrin antibody is more effective at treating one or more symptoms of IBD compared to either compound/antibody alone.

1. Chemokine Receptor Type (CCR9) Inhibitors

The present invention provides compounds that modulate CCR9 activity. Specifically, the invention provides compounds having anti-inflammatory or immunoregulatory activity. The compounds of the invention are thought to interfere with inappropriate T-cell trafficking by specifically modulating or inhibiting a chemokine receptor function. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor-ligand interaction, can inhibit or reduce a chemokine receptor mediated response, as wells as treat or prevent a chemokine receptor mediated condition or disease.

Without being bound by any particular theory, it is believed that the compounds provided herein interfere with the interaction between CCR9 and its ligand CCL25. For example, compounds of this invention act as potent CCR9 antagonists, and this antagonistic activity has been further confirmed in animal testing for inflammation, one of the hallmark disease states for CCR9. Compounds contemplated by the invention include, but are not limited to, the exemplary compounds provided herein and salts thereof.

For example, useful compounds act as potent CCR9 antagonists, and this antagonistic activity has been further confirmed in animal testing for inflammation, one of the hallmark disease states for CCR9. Accordingly, the compounds provided herein are useful in pharmaceutical compositions and methods for the treatment of inflammatory bowel disease, e.g., ulcerative colitis and Crohn's disease.

In some embodiments, CCR9 inhibitors, e.g., CCR9 small molecule inhibitors of the present disclosure are represented by formula (I), or salts thereof:

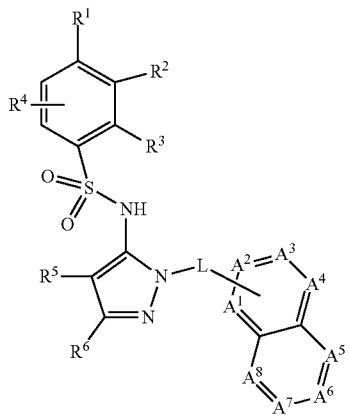

(I)

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl, and;

$R^2$ is H, F, Cl, or substituted or unsubstituted $C_{1-8}$ alkoxy; or $R^1$ and $R^2$ together with the carbon atoms to which they are attached form a non-aromatic carbocyclic ring or a heterocyclic ring;

$R^3$ is H, substituted or unsubstituted $C_{1-8}$ alkyl, substituted or unsubstituted $C_{1-8}$ alkoxy, or halo;

$R^4$ is H or F;

$R^5$ is H, F, Cl, or —$CH_3$;

$R^6$ is H, halo, —CN, —$CO_2R^a$, —$CONH_2$, —$NH_2$, substituted or unsubstituted $C_{1-8}$ alkyl, substituted or unsubstituted $C_{1-8}$ alkoxy, or substituted or unsubstituted $C_{1-8}$ aminoalkyl;

$R^a$ is H or substituted or unsubstituted $C_{1-8}$ alkyl;

where $R^5$ and $R^6$ may together form a carbocyclic ring;

L is a bond, —$CH_2$—, or —$CH(CH_3)$—;

each of $A^1$, $A^2$, $A^3$, $A^4$, $A^5$, $A^6$, $A^7$, and $A^8$ are independently selected from the group consisting of N, N—O, and —$CR^8$—; where at least one and not more than two of $A^1$, $A^2$, $A^3$, $A^4$, $A^5$, $A^6$, $A^7$, and $A^8$ are N or N—O;

$R^8$ is each independently selected from the group consisting of H, halo, —CN, —OH, oxo, substituted or unsubstituted $C_{1-8}$ alkyl, substituted or unsubstituted $C_{1-8}$ alkoxy, and $NR^{20}R^{21}$, substituted or unsubstituted aryl, substituted or unsubstituted heteroaryl, and substituted or unsubstituted heterocyclyl; and $R^{20}$ and $R^{21}$ are each independently H, or substituted or unsubstituted $C_{1-8}$ alkyl.

In some embodiments of formula (I), one of $A^1$ or $A^2$ is N or N—O, and the remaining of $A^1$, $A^2$, $A^3$, $A^4$, $A^5$, $A^6$, $A^7$, and $A^8$ are —$CR^8$—, where each $R^8$ is selected independently.

In some embodiments, two of, $A^2$, $A^3$, $A^4$, $A^5$ is N or N—O, and the remaining of $A^1$, $A^2$, $A^3$, $A^4$, $A^5$, $A^6$, $A^7$, and $A^8$ are —$CR^8$—, where each $R^8$ is selected independently.

In some embodiments, the compounds or compositions of formula (I) are represented by formula (II) or salts thereof:

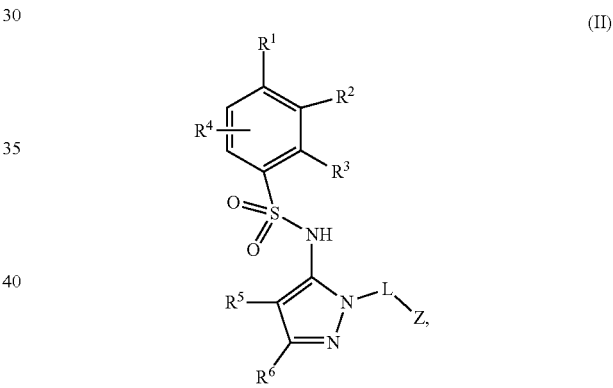

(II)

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl;

$R^2$ is H, F, Cl, or substituted or unsubstituted $C_{1-8}$ alkoxy; or $R^1$ and $R^2$ together with the carbon atoms to which they are attached form a non-aromatic carbocyclic ring or a heterocyclic ring;

$R^3$ is H, substituted or unsubstituted $C_{1-8}$ alkyl, substituted or unsubstituted $C_{1-8}$ alkoxy, or halo;

$R^4$ is H or F;

$R^5$ is H, F, Cl, or —$CH_3$;

$R^6$ is H, halo, —CN, —$CO_2R^a$, —$CONH_2$, —$NH_2$, substituted or unsubstituted $C_{1-8}$ aminoalkyl, substituted or unsubstituted $C_{1-8}$ alkyl, or substituted or unsubstituted $C_{1-8}$ alkoxy;

$R^a$ is H or substituted or unsubstituted $C_{1-8}$ alkyl;

where $R^5$ and $R^6$ may together form a carbocyclic ring;

L is a bond, —$CH_2$—, or —$CH(CH_3)$—; and

Z is selected from the group consisting of:

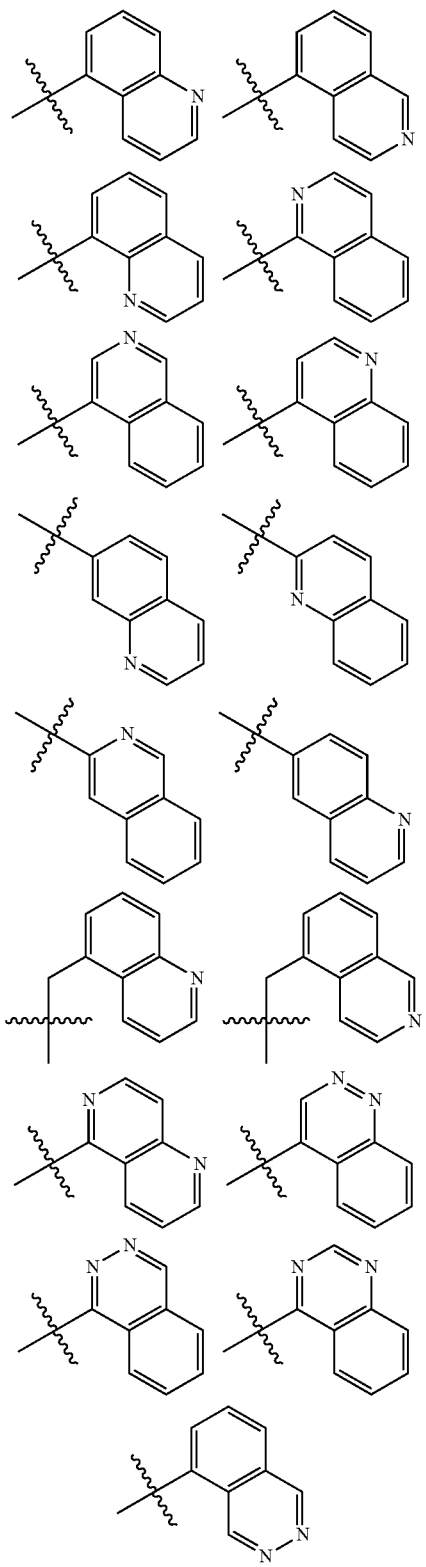

and N-oxides thereof;

where the Z group may be unsubstituted or substituted with 1 to 3 independently selected $R^8$ substituents;

each $R^8$ is independently selected from the group consisting of H, halo, —CN, —OH, oxo, substituted or unsubstituted $C_{1-8}$ alkyl, substituted or unsubstituted $C_{1-8}$ alkoxy, and $NR^{20}R^{21}$, substituted or unsubstituted aryl, substituted or unsubstituted heteroaryl, and substituted or unsubstituted heterocyclyl; and $R^{20}$ and $R^{21}$ are each independently H, substituted or unsubstituted $C_{1-8}$ alkyl.

In some embodiments of formula (II), Z is selected from the group consisting of: substituted or unsubstituted quinolinyl, substituted or unsubstituted isoquinolinyl, substituted or unsubstituted 1,6-naphthyridinyl, substituted or unsubstituted cinnolinyl, substituted or unsubstituted phthalazinyl, substituted or unsubstituted quinazolinyl.

In one embodiment, the compounds or compositions of formula (I) provided herein are represented by formula (IIIa) or (IIIb), or salts thereof:

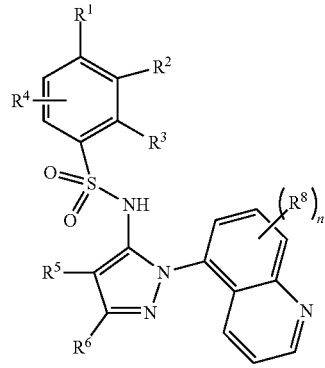
(IIIa)

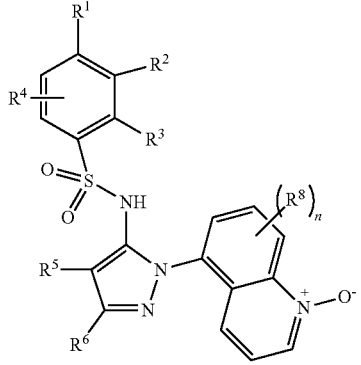
(IIIb)

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl;

$R^2$ is H, F, Cl, or substituted or unsubstituted $C_{1-8}$ alkoxy; or $R^1$ and $R^2$ together with the carbon atoms to which they are attached form a non-aromatic carbocyclic ring or a heterocyclic ring;

$R^3$ is H, substituted or unsubstituted $C_{1-8}$ alkyl, substituted or unsubstituted $C_{1-8}$ alkoxy, or halo;

$R^4$ is H or F;

$R^5$ is H, F, Cl, or —CH$_3$;

$R^6$ is H, halo, —CN, —CO$_2$R$^a$, —CONH$_2$, —NH$_2$, substituted or unsubstituted $C_{1-8}$ aminoalkyl, substituted or unsubstituted $C_{1-8}$ alkyl, or substituted or unsubstituted $C_{1-8}$ alkoxy;

$R^a$ is H or substituted or unsubstituted $C_{1-8}$ alkyl;

or where $R^5$ and $R^6$ together with the carbon atoms to which they are attached form a carbocyclic ring;

each $R^8$ is independently selected from the group consisting of H, halo, —CN, —OH, oxo, substituted or unsubstituted $C_{1-8}$ alkyl, substituted or unsubstituted $C_{1-8}$ alkoxy, and $NR^{20}R^{21}$, substituted or unsubstituted aryl, substituted or unsubstituted heteroaryl, and substituted or unsubstituted heterocyclyl;

$R^{20}$ and $R^{21}$ are each independently H, or substituted or unsubstituted $C_{1-8}$ alkyl; and n is 0, 1, 2 or 3.

In one embodiment of formula (IIIa) or (IIIb) or salts thereof, $R^1$ is selected from the group consisting of: —CH$_2$CH$_3$, —CH(CH$_3$)$_2$, —C(CH$_3$)$_3$, —C(CH$_3$)$_2$CH$_2$CH$_3$, —C(CH$_2$CH$_2$)CN, —C(OH)(CH$_3$)$_2$, —OCH$_3$, —OCH$_2$CH$_3$, —OCH(CH$_3$)$_2$, —OC(CH$_3$)$_3$, —OCH$_2$CH(CH$_3$)$_2$, —OCF$_3$, and morpholino; $R^2$ is H, F, or Cl; or $R^1$ and $R^2$ may together form —OC(CH$_3$)$_2$CH$_2$— or —C(CH$_3$)$_2$CH$_2$CH$_2$—; $R^3$ is H, —CH$_3$, or —OCH$_3$; $R^4$ is H or F; $R^5$ is H; $R^6$ is H, —CH$_3$, —CH$_2$CH$_3$, —CH(CH$_3$)$_2$, —C$_3$H$_7$, —CH$_2$F, —CHF$_2$, —CF$_2$CH$_3$, —CF$_3$, —CH$_2$OCH$_3$, —CH$_2$OH, —CH$_2$CN, —CN, or —CONH$_2$; and each $R^8$ is independently selected from the group consisting of H, F, Cl, Br, —CH$_3$, —OH, —OCH$_3$, —OCH$_2$CH$_3$, —NH$_2$, —N(CH$_3$)$_2$, and —CN. In some instances, $R^1$ is —C(CH$_3$)$_3$.

In other embodiments of formula (IIIa) or formula (IIIb), $R^2$ is H or F; $R^3$ is H; $R^4$ is H; and $R^6$ is —CH$_3$, —CH$_2$F, —CHF$_2$, or —CF$_3$.

In one embodiment, the compounds and compositions of formula (IIIa) or (IIIb) or salts thereof are selected from the group consisting of:

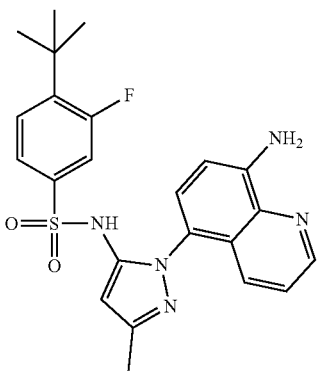

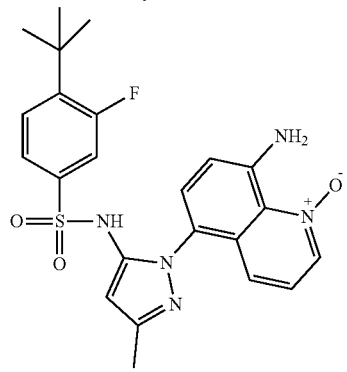

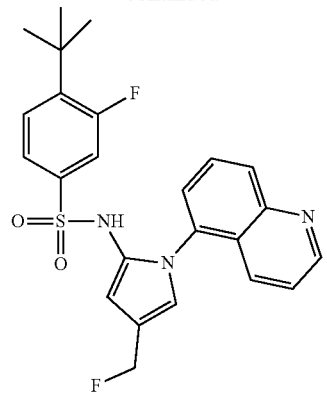

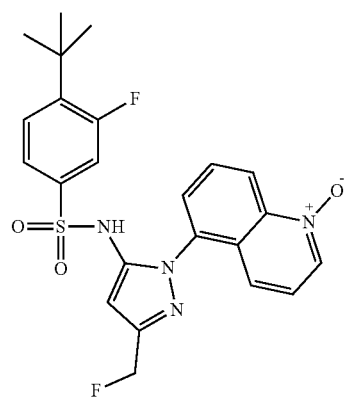

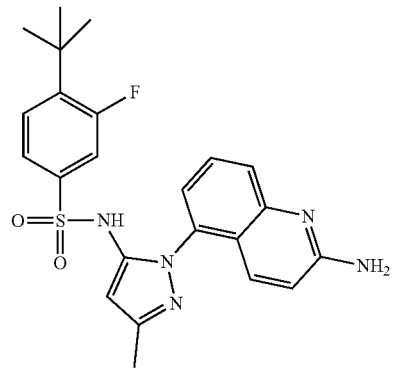

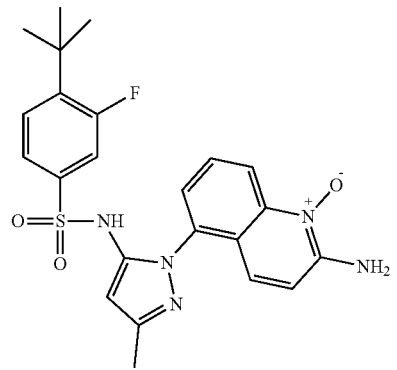

23
-continued

24
-continued

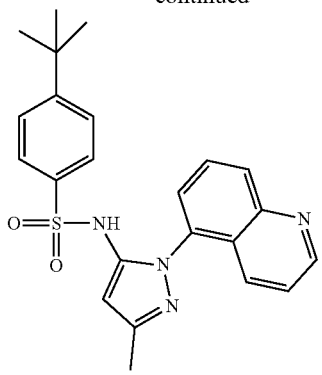
and
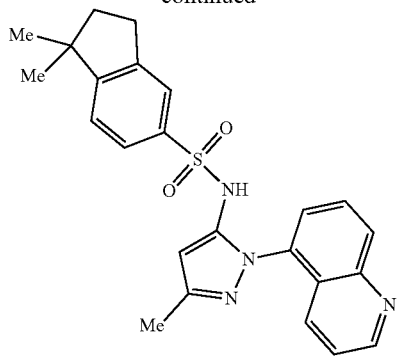
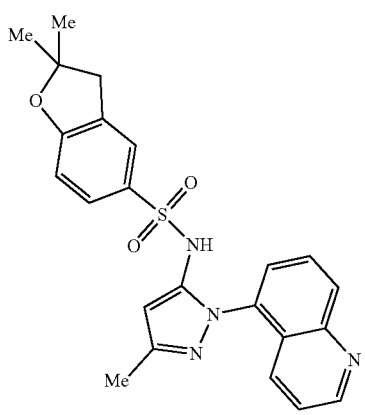
In some embodiments, CCR9 inhibitors, e.g., CCR9 small molecule inhibitor compounds and compositions provided herein are selected from the group consisting of:
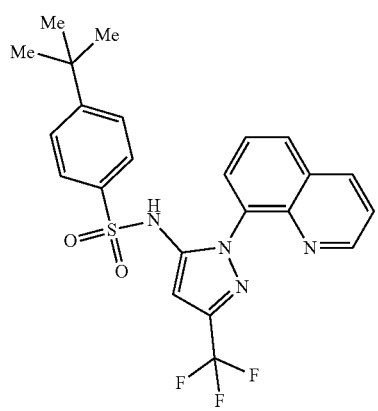
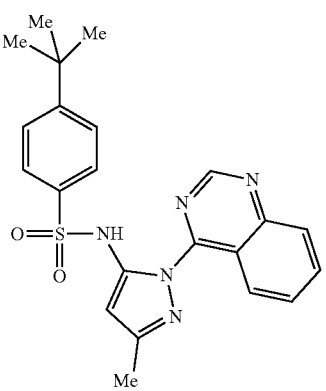
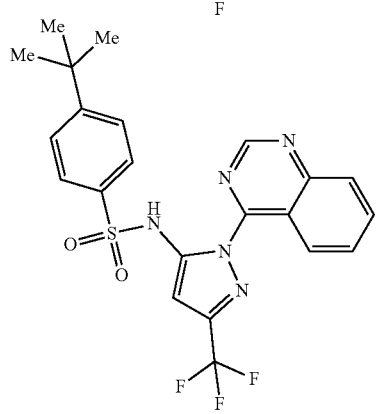
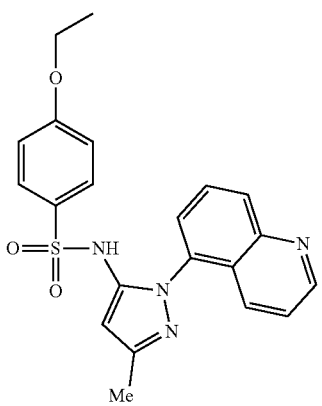

-continued

29
-continued
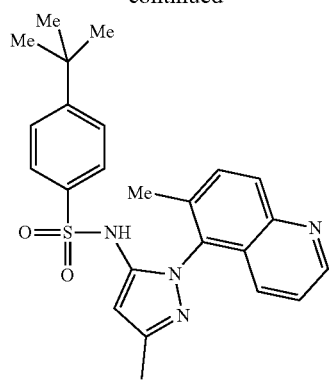
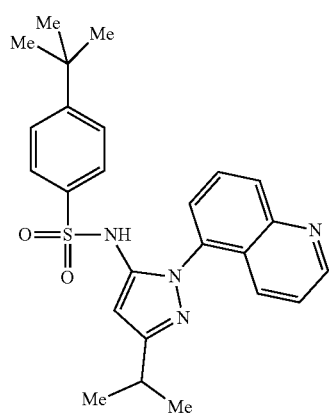
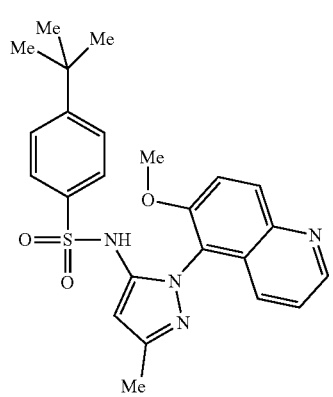
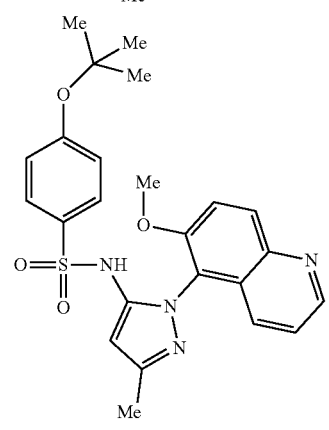
30
-continued
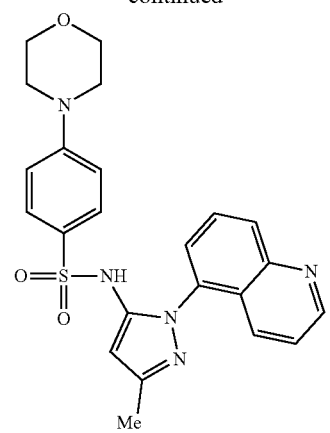
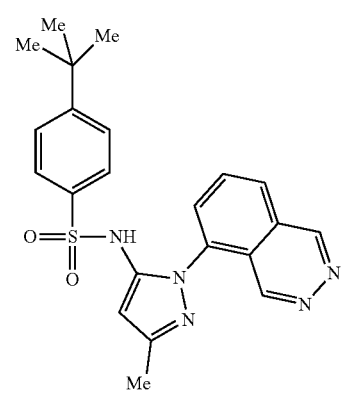
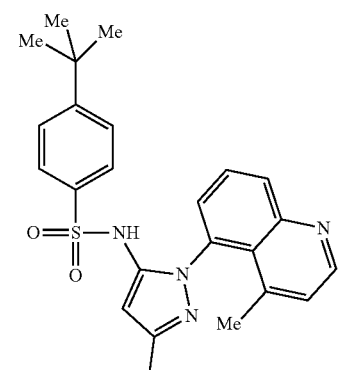
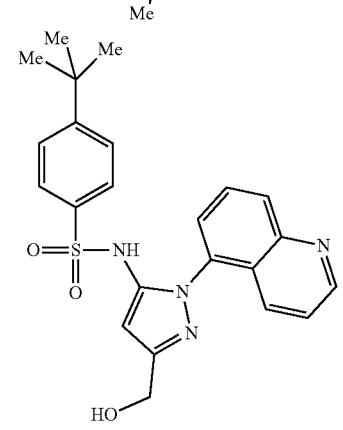

-continued
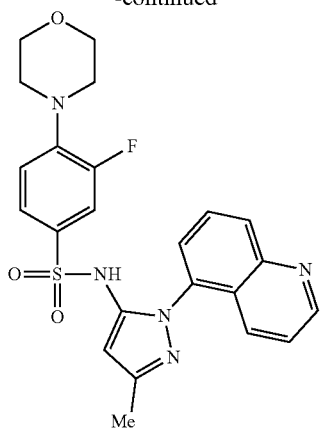
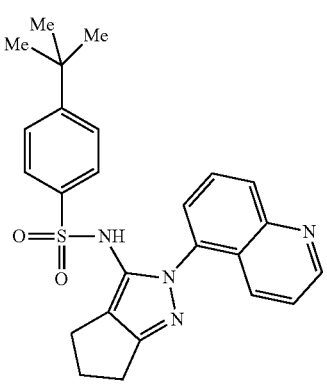
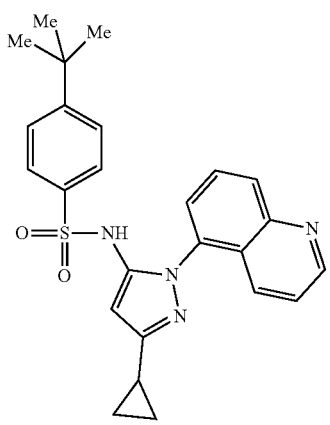
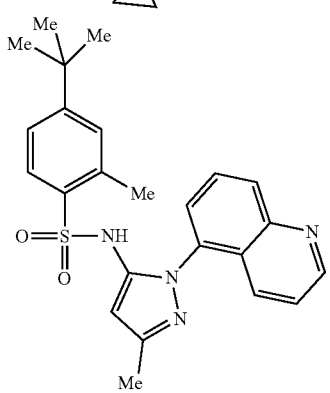
-continued
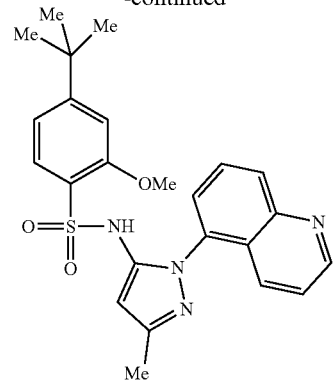
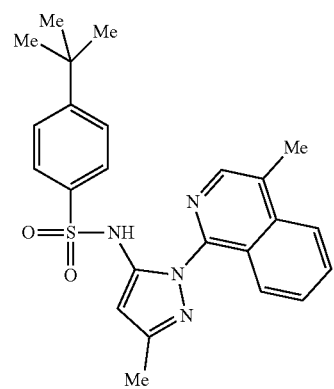
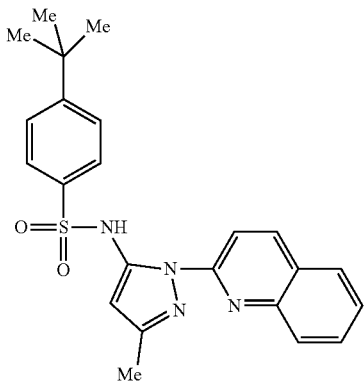
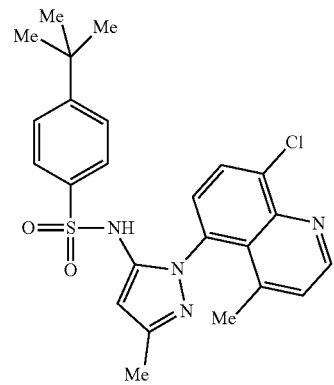

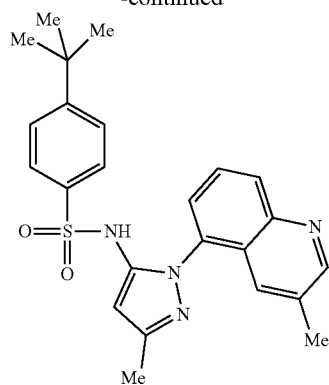
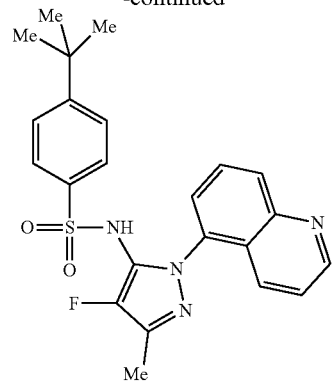
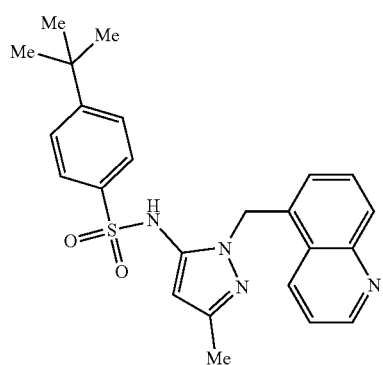
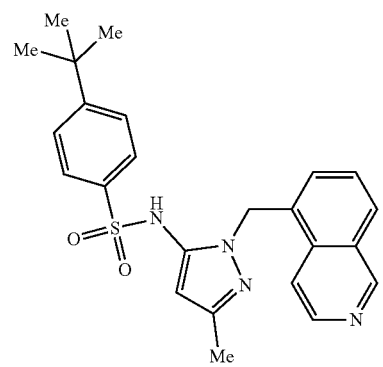
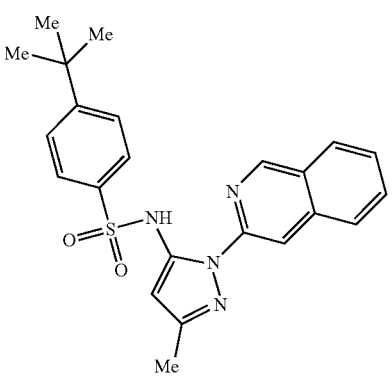

-continued
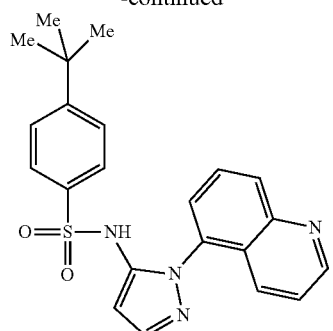
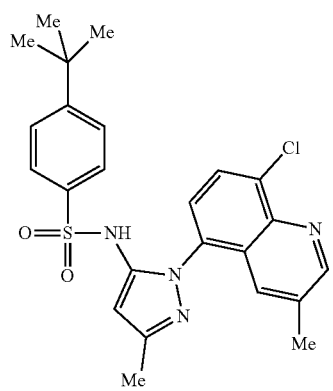
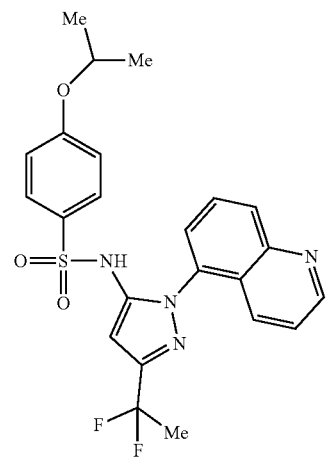
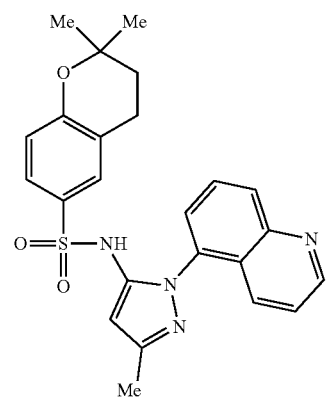
-continued
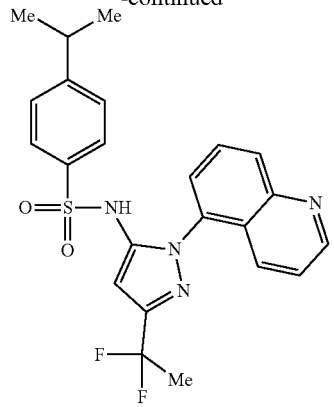
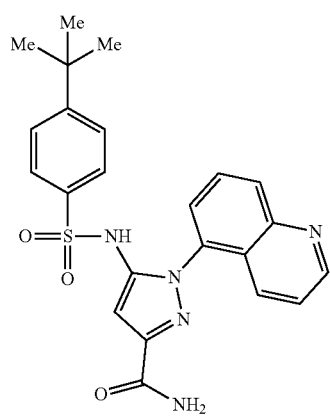
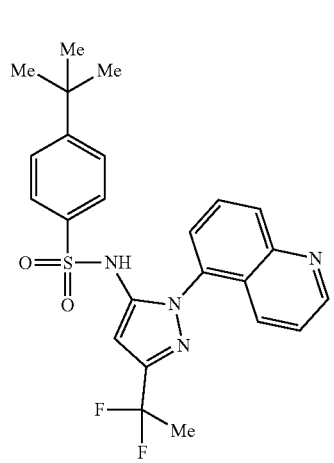
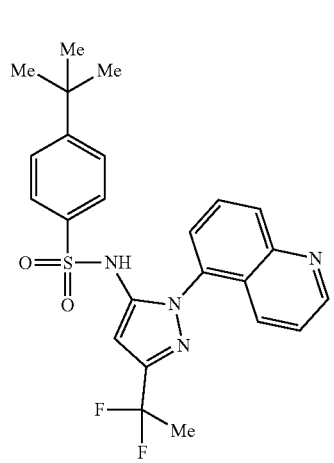

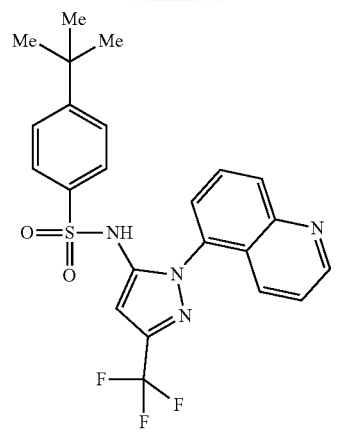
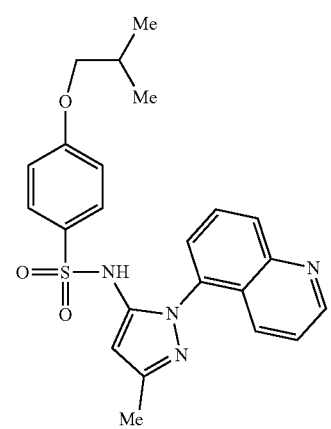
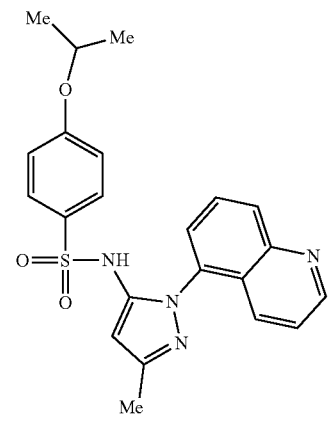
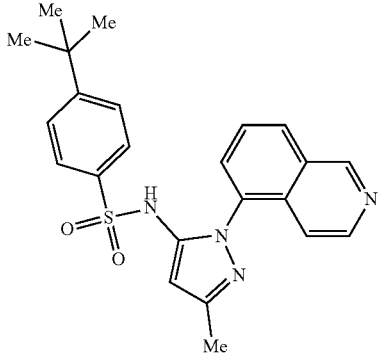
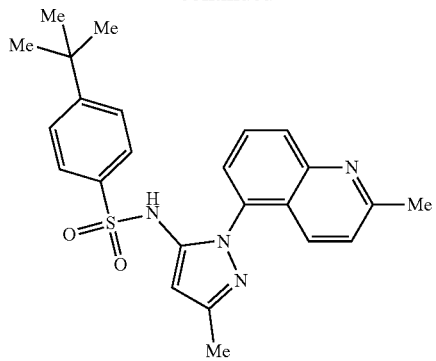
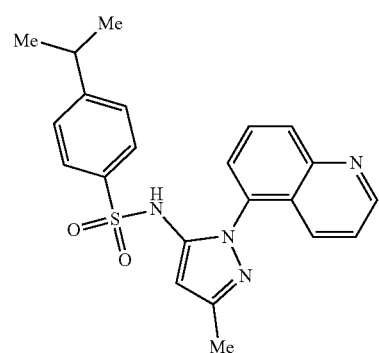
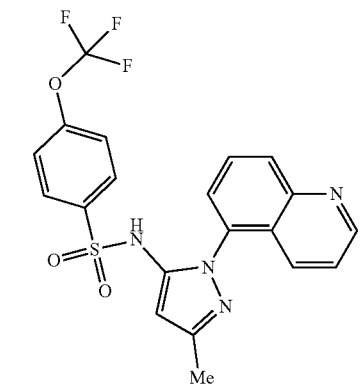
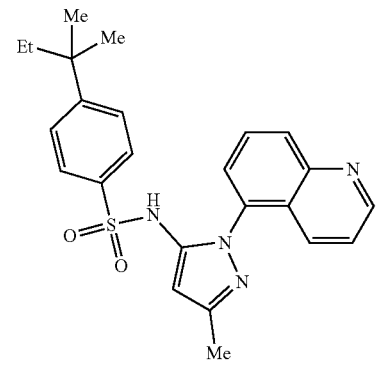

-continued
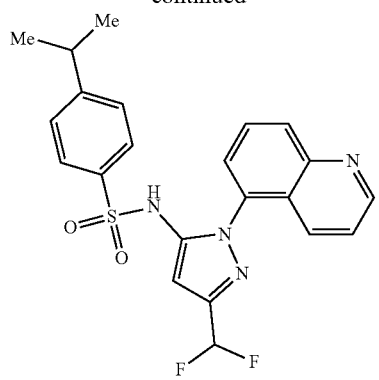
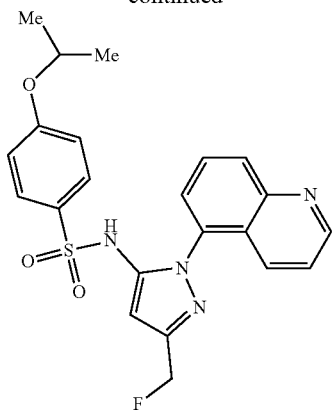
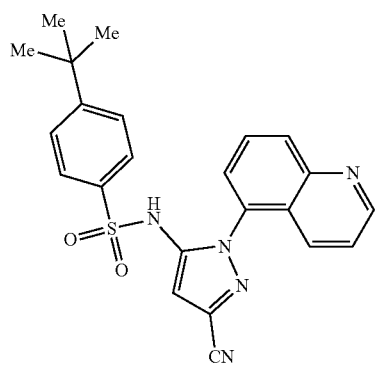
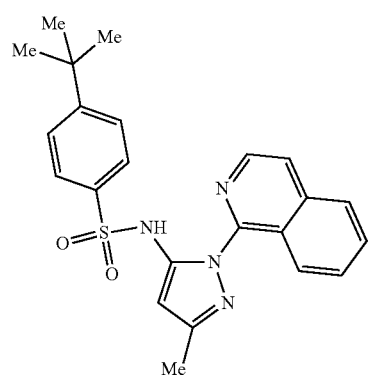
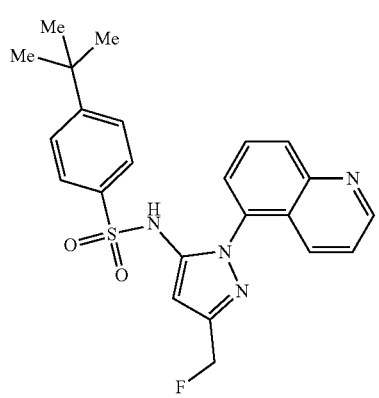
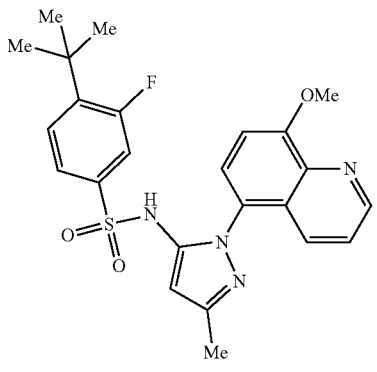
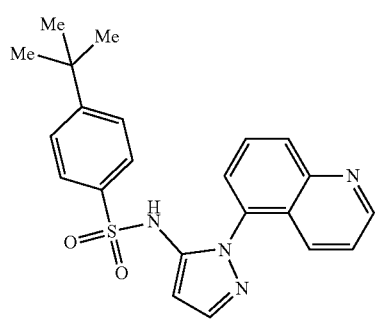
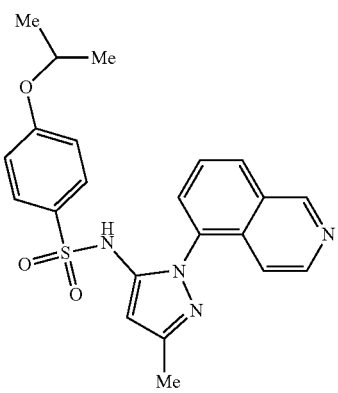

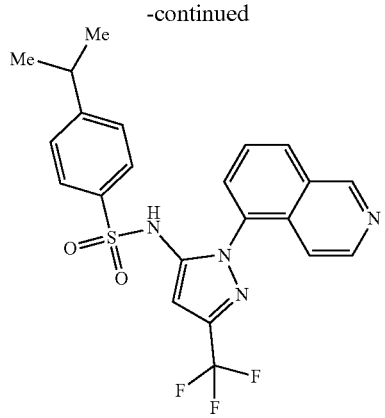
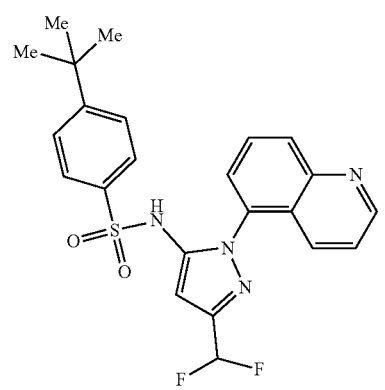
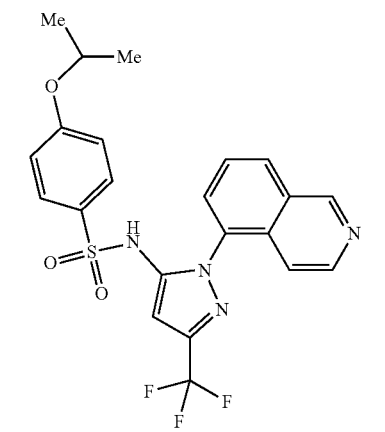
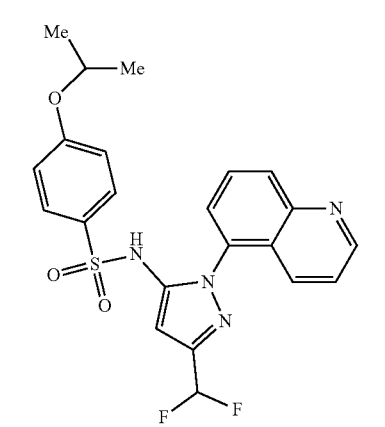
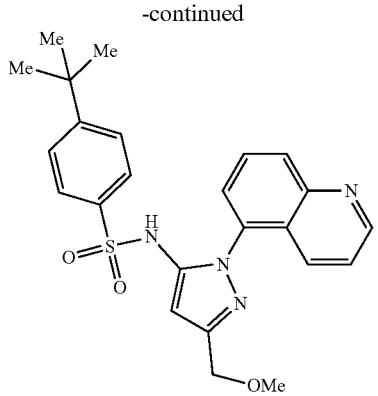
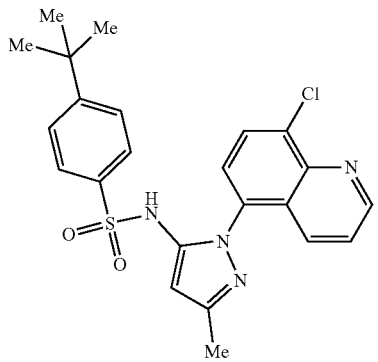
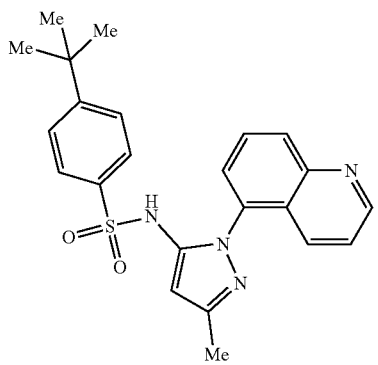
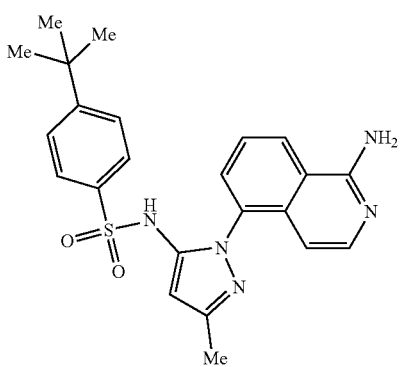

-continued
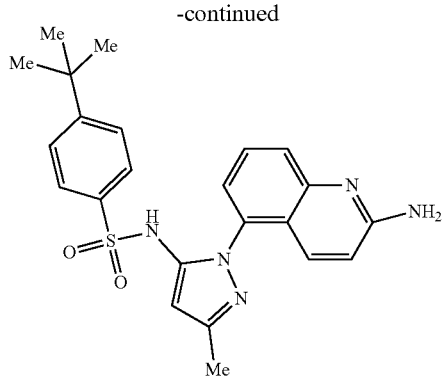
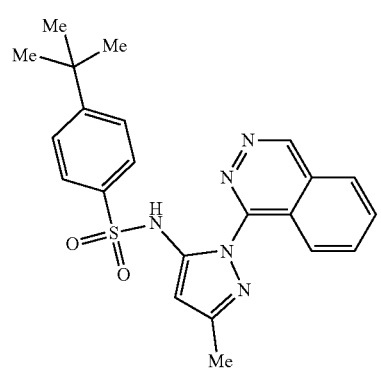
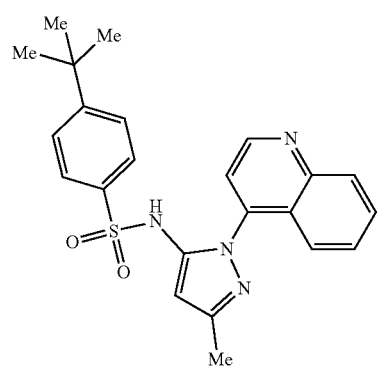
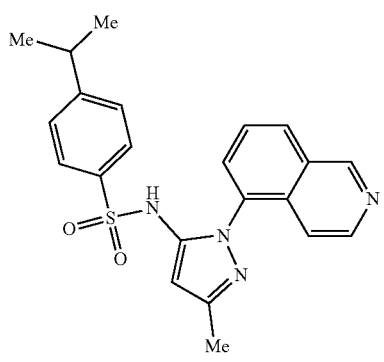
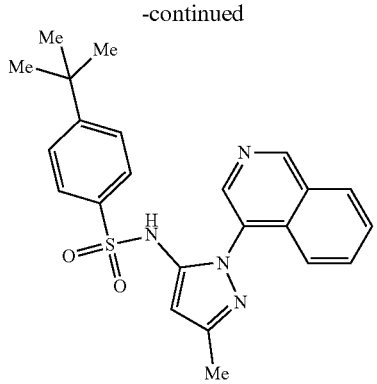
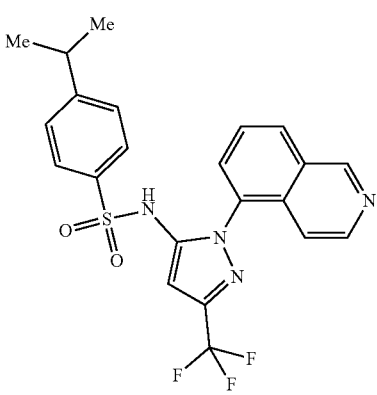
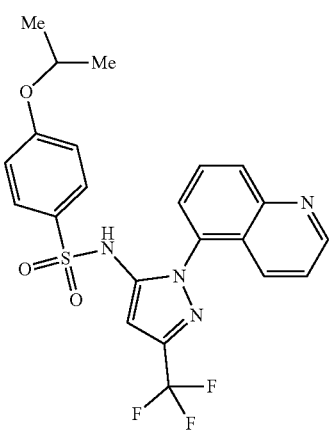

45
-continued
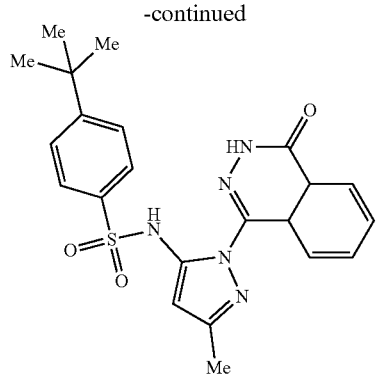
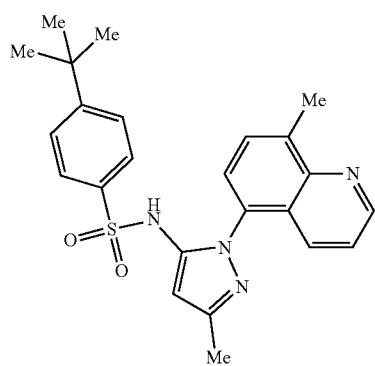
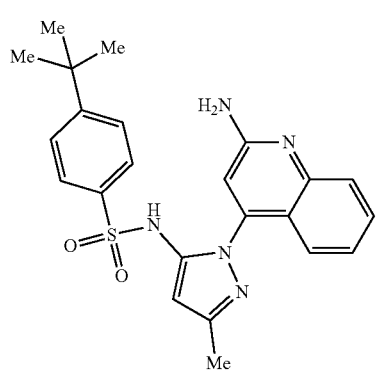
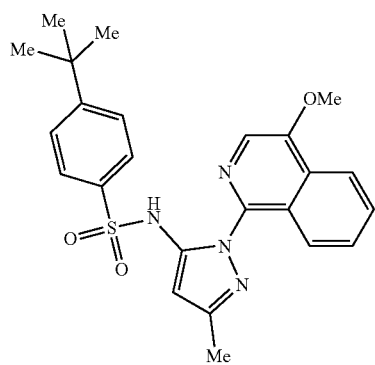
46
-continued
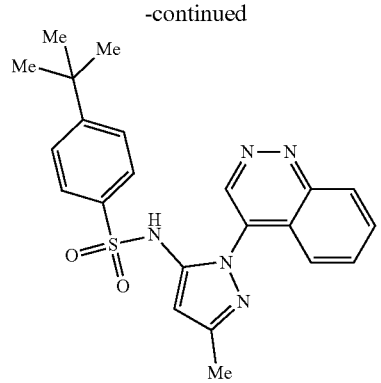
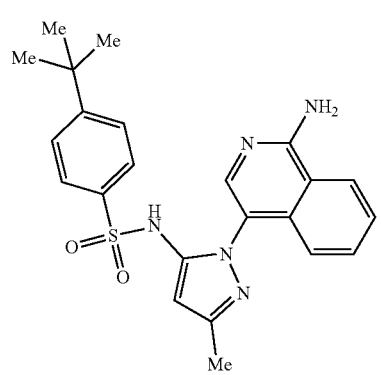
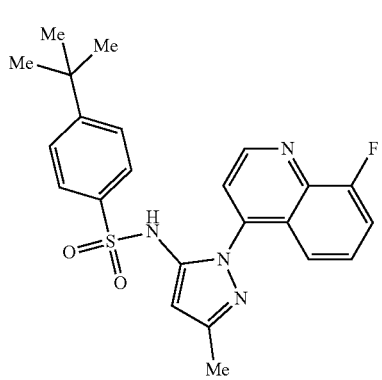
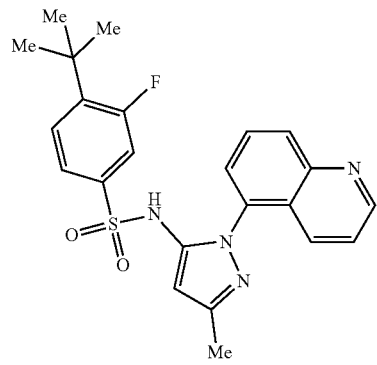

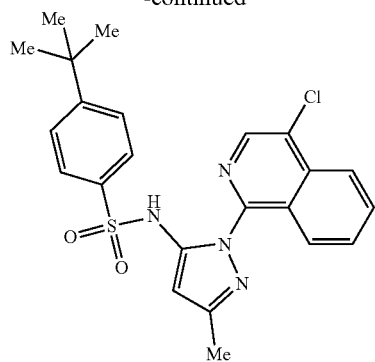
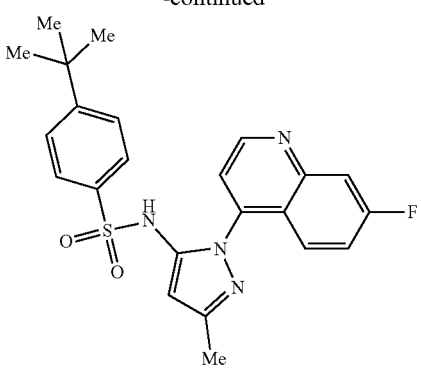
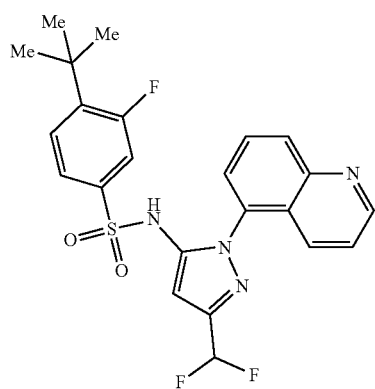
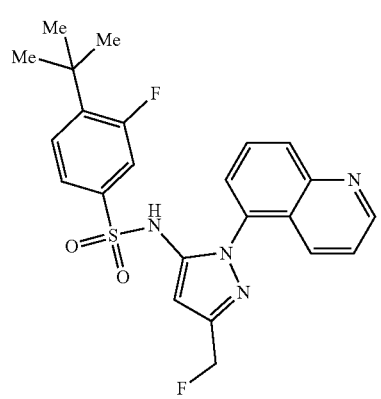
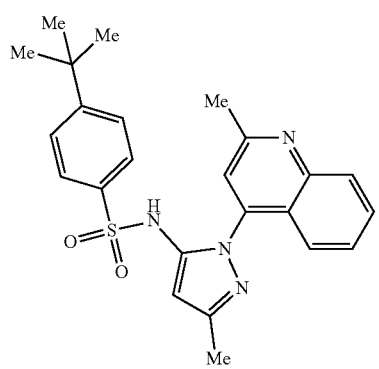
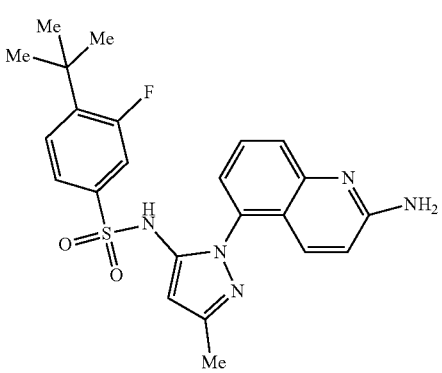
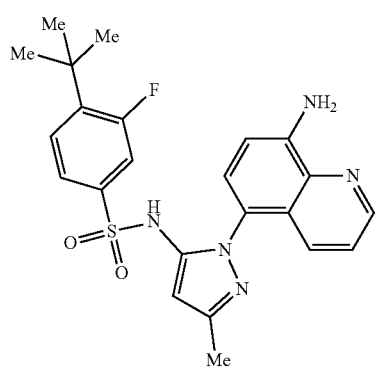
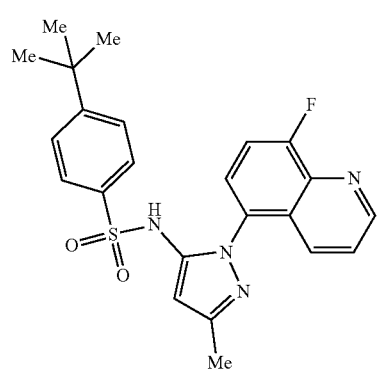

49
-continued
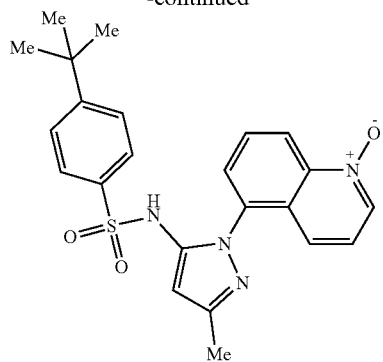
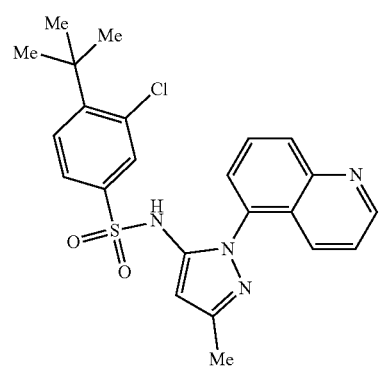
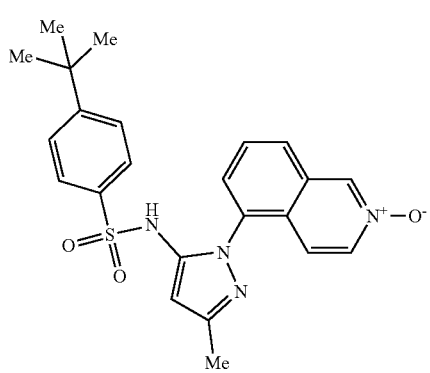
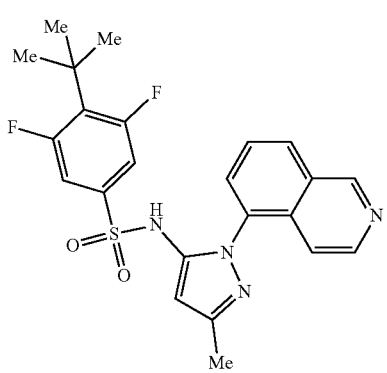
50
-continued
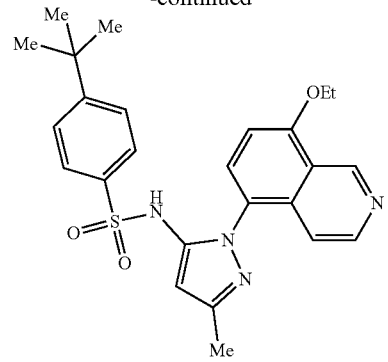
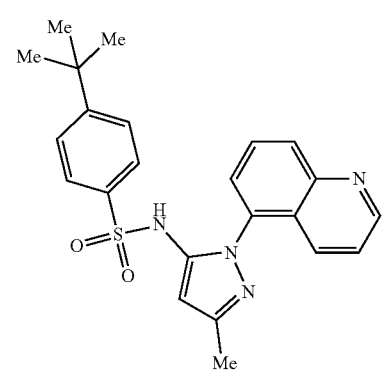
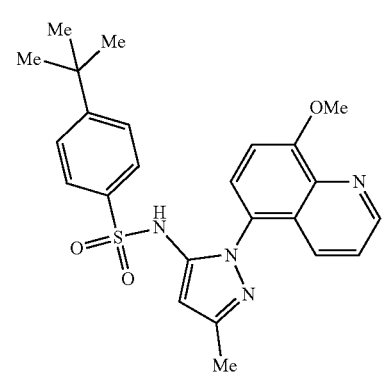
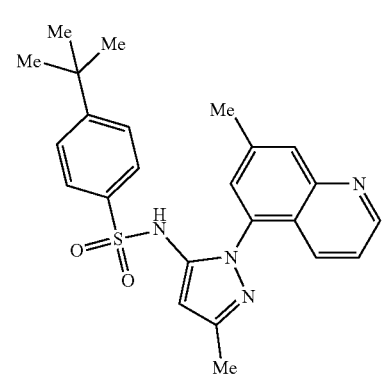

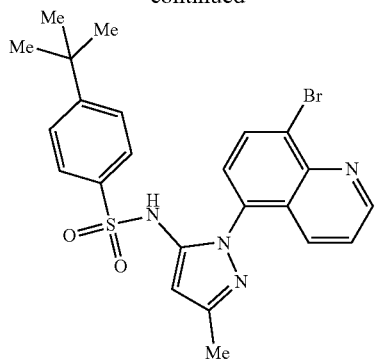
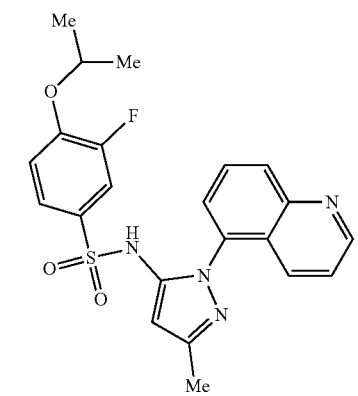
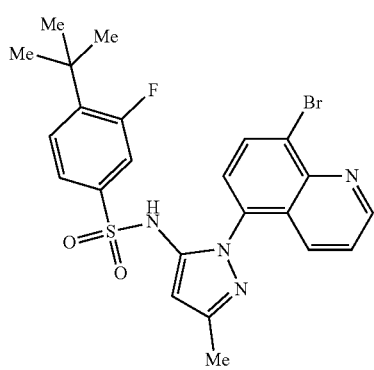
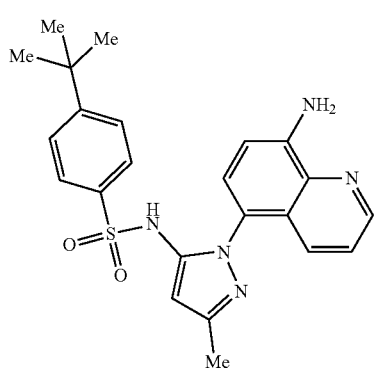
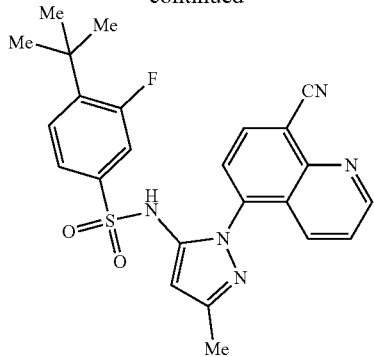
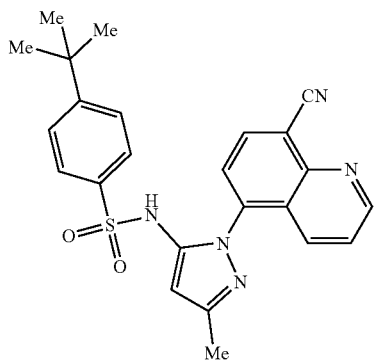

and N-oxides thereof.

In some embodiments, the preferred $R^1$ substituents are as follows. In formula (I, II, IIIa, and IIIb), $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl. When $R^1$ is substituted alkyl, the alkyl group is preferably substituted with halo or hydroxy. When $R^1$ is substituted alkoxy, the alkoxy group is preferably substituted with halo. Preferably $R^1$ is unsubstituted $C_{2-8}$ alkyl, including $C_{3-8}$ cycloalkyl, $C_{2-8}$ haloalkyl, $C_{1-8}$ hydroxyalkyl, unsubstituted $C_{1-8}$ alkoxy, $C_{1-8}$ haloalkoxy, and $C_{1-8}$ alkylamino; more preferably unsubstituted $C_{2-8}$ alkyl, $C_{2-8}$ haloalkyl, unsubstituted $C_{1-8}$ alkoxy, and $C_{1-8}$ alkylamino; even more preferably unsubstituted $C_{2-8}$ alkyl, unsubstituted $C_{1-8}$ alkoxy, and morpholino; still more preferably unsubstituted $C_{2-8}$; and most preferably t-butyl.

In some embodiments, the preferred $R^6$ substituents are as follows. In formula (I, II, IIIa, and IIIb), $R^6$ is H, halo, —CN, —CO$_2$R$_a$, —CONH$_2$, —NH$_2$, substituted or unsubstituted $C_{1-8}$ alkyl, substituted or unsubstituted $C_{1-8}$ alkoxy, or substituted or unsubstituted $C_{1-8}$ aminoalkyl. When $R^6$ is substituted alkyl, the alkyl group is preferably substituted with halo, hydroxy, alkoxy, or cyano. Preferably $R^6$ is —CN, —CONH$_2$, —NH$_2$, unsubstituted $C_{1-8}$ alkyl, unsubstituted $C_{1-8}$ haloalkyl, and unsubstituted $C_{1-8}$ alkoxy; more preferably unsubstituted $C_{1-8}$ alkyl, or unsubstituted $C_{1-8}$ haloalkyl, even more preferably unsubstituted $C_{1-8}$ alkyl; most preferably methyl.

In some embodiments, the CCR9 small molecule inhibitor compound of the present invention is

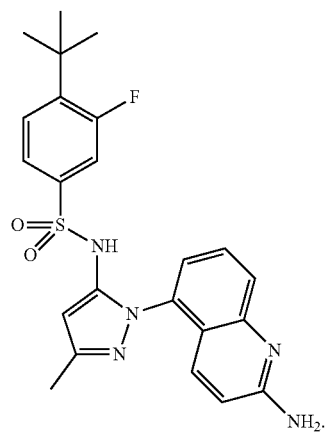 [SMILES: Cc1cc(NS(=O)(=O)c2ccc(C(C)(C)C)c(F)c2)n(-c2cccc3nc(N)ccc23)n1]

In one embodiment, the CCR9 small molecule inhibitor is vercirnon (Traficet-EN™) or CCX507.

Detailed descriptions of the CCR9 inhibitor compounds provided herein and methods for preparing such compounds is found in, for example, U.S. Pat. No. 8,916,601 and U.S. Patent Application Publication Nos. 2013/0267492, 2013/0059893, 2012/0245138, 2012/0165303, 2011/0021523, 2010/0331302, 2010/0227902, 2010/0190762, 2010/0152186, 2010/0056509, 2009/0163498 and 2009/0005410, the disclosures of which are herein incorporated by reference in their entirety for all purposes.

The compounds provided herein may be may be synthesized using a variety of standard organic chemistry transformations. Certain general reaction types employed widely to synthesize target compounds in this invention are summarized in the examples. Specifically, generic procedures for sulfonamide formation and aza-aryl N-oxide formation are described within and were employed routinely.

While not intended to be exhaustive, representative synthetic organic transformations which can be used to prepare compounds of the invention are included herein. These representative transformations include; standard functional group manipulations; reductions such as nitro to amino; oxidations of functional groups including alcohols and aza-aryls; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention. In particular, when $R^8$ is OH and ortho to a nitrogen, although illustrated by formula as —N═C(OH)— it is to be understood that the tautomeric form —NH—C(O)— is also within the scope of the formula.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

2. Pharmaceutical Formulations of CCR9 Inhibitors

In another aspect, the present disclosure provides compositions or formulations that modulate CCR9 activity. Generally, the compositions or formulations for modulating chemokine receptor activity in a subject such as a human or animal will comprise a compound provided herein and a pharmaceutically acceptable excipient or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients.

In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

In some embodiments, the CCR9 inhibitor of the present disclosure is a pharmaceutical compound having a crystalline form. A non-limiting example of such a crystalline form of a CCR9 inhibitor is described in, e.g., U.S. Pat. No. 9,133,124, the disclosure of which is herein incorporated by reference in its entirety for all purposes.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,399, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where the active ingredient is mixed with an inert solid diluent, for example, calcium carbonate, calcium phosphate or kaolin, or as soft gelatin capsules where the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds disclosed herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered viaocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

3. Anti-α4β7 Integrin Blocking Antibodies

Anti-α4β7 integrin antibodies suitable for use in the treatment of inflammatory bowel disease, e.g., Crohn's disease and ulcerative colitis include antibodies from any desired source that inhibits the binding of α4β7 integrin to any one of its ligands such as mucosal addressin (MadCAM-1), fibronectin, vascular cell adhesion molecule (VCAM), and the like. Anti-α4β7 integrin antibodies can be human antibodies, mouse antibodies, rabbit antibodies, engineered antibodies such as chimeric antibodies, humanized antibodies, and antigen-binding fragments of antibodies such as Fab, Fv, scFv, Fab' and F(ab')$_2$ fragments.

In some embodiments, the anti-α4β7 integrin antibody binds to an epitope on the α4 chain, an epitope on the β7 chain, or a composite epitope formed by the association of the α4 chain and the β7 chain. In some cases, the anti-α4β7 integrin antibody binds an epitope formed by the association of the α4 and β7 chains, and does not bind an epitope on the α4 chain or on the β7 chain, if the α4 and β7 chain are not associated or complexed together.

Non-limiting examples of an anti-α4β7 integrin antibody for use in the method described herein include vedolizumab (ENTYVIO®), natalizumab (Tysabri®), AMG 181 (Amgen) and those described in, e.g., International Patent Publication No. WO 2012/151248, U.S. Pat. Nos. 7,147,851; 7,402,410; 8,444,981; 8,454,961; 8,454,962; 8,871,490; and U.S. Patent Application Publication No. 2015/0086563, the disclosures of which are herein incorporated by reference in their entirety for all purposes. Additional useful anti-α4β7 integrin antibodies include bioequivalents, biosimilars, and biobetters of any of the anti-α4β7 integrin antibodies described herein.

In some embodiments, the anti-α4β7 integrin antibody of the present disclosure is an antibody with an amino acid sequence that has at least 70%, at least 80%, at least 90%, at least 95% or more sequence identity to an anti-α4β7 integrin reference antibody such as vedolizumab, AMG 181 or other anti-α4β7 integrin antibody that is known to one skilled in the art. In some instances, the antibody variant has one or more amino acid substitutions, deletions and/or additions at certain amino acid positions of the reference antibody, but retains antigen binding activity.

One of skill in the art recognizes that "percent of sequence identity" can determined by comparing two optimally aligned sequences over a comparison window or designated region of the sequence, wherein the portion of the polypeptide sequence in the comparison window may comprise additions or deletions (i.e., gaps) as compared to the reference sequence (which does not comprise additions or deletions) for optimal alignment of the two sequences. The percentage can be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Percent sequence identity can be measured using a BLAST or BLAST 2.0 sequence comparison algorithms, with default parameters, or by manual alignment and visual inspection.

Antibodies, fragments thereof, variants thereof and derivatives thereof may be generated using a variety of standard methods recognized by those skilled in the art. See, e.g., Harlow, E. and Lane DP. Antibodies: A Laboratory Manual. Cold Spring Harbor: Cold Spring Harbor Laboratory Press, 1988. Antigen-binding fragments such as Fab and F(ab')$_2$ fragments may be produced by genetic engineering. Procedures for the production of chimeric and further engineered monoclonal antibodies include those described in Riechmann et al., *Nature*, 1988,332:323, Liu et al., *Proc. Nat. Acad. Sci. USA*, 1987, 84:3439, Larrick et al., *Bio/Technology*, 1989, 7:934, and Winter et al., *TIPS*, 1993, 14:139. Examples of techniques for production and use of transgenic animals for the production of human or partially human antibodies are described in, e.g., Davis et al., 2003, Production of human antibodies from transgenic mice in Lo, ed. Antibody Engineering Methods and Protocols, Humana Press, NJ:191-200.

4. Pharmaceutical Formulations of Anti-α4β7 Integrin Antibodies

Provided herein are formulations of the anti-α4β7 integrin antibody that can stabilize the antibody, reduce the formation of antibody aggregates, retard the degradation of the antibody, and/or minimize the immunogenicity of the antibody. The formulation can include an antioxidant or chelator, at least one free amino acid, a surfactant, a non-reducing sugar, and/or a buffering agent.

The antioxidant or chelator can be citrate, ethylenediaminetetraacetic acid (EDTA), ethyleneglycoltetraacetic acid (EGTA), dimercaprol, diethylenetriaminepentaacetic acid, or N,N-bis(carboxymethyl)glycine; preferably citrate or EDTA. The free amino acid can be histidine, alanine, arginine, glycine, glutamic acid and combinations thereof. The surfactant can be polysorbates 20; polysorbate 80; TRITON (t-octylphenoxypolyethoxyethanol, nonionic detergent; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; sorbitan monopalmitate; polyethyl glycol (PEG), polypropylene glycol (PPG), and copolymers of poloxyethylene and poloxypropylene glycol; preferably polysorbates 80.

The buffering agent can be a buffer that can adjust the pH of the formulation to about 5.0 to about 7.5, to about pH 5.5 to about 7.5, to about pH 6.0 to about 7.0, or to a pH of about 6.3 to about 6.5. Non-limiting examples of a buffering agent include acetate, succinate, gluconate, histidine, citrate, phosphate, maleate, cacodylate, 2-[N-morpholino]ethanesulfonic acid (MES), bis(2-hydroxyethyl)iminotris[hydroxymethyl]methane (Bis-Tris), N-[2-acetamido]-2-iminodiacetic acid (ADA), glycylglycine and other organic acid buffers, preferably histidine or citrate.

In some embodiments, the anti-α4β7 integrin antibody is in a lyophilized formulation, e.g., a dry form. In some cases, the lyophilized formulation includes the anti-α4β7 integrin antibody and one or more excipients, such as a non-reducing sugar, a buffering agent, a free amino acid, and/or a surfactant.

In some cases, the lyophilized formulation contains at least about 50 mg, at least about 60 mg, at least about 70 mg, at least about 80 mg, at least about 90 mg, at least about 100 mg, at least about 120 mg, at least about 140 mg, at least about 180 mg, at least about 200 mg, at least about 220 mg, at least about 240 mg, at least about 280 mg, at least about 300 mg, at least about 400 mg, at least about 500 mg, at least about 600 mg, at least about 700 mg, at least about 800 mg, at least about 900 mg of anti-α4β7 integrin antibody. In some cases, the lyophilized formulation is stored as a single dose in one vial.

In some embodiments, the anti-α4β7 integrin antibody is a liquid formulation. Such a formulation can include the anti-α4β7 integrin antibody, a buffering agent, a non-reducing sugar, and/or a free amino acid.

The amount of antibody present in a liquid formulation can be at least about 25 mg/ml to about 200 mg/ml anti-α4β7 integrin antibody, e.g., 25 mg/ml to about 200 mg/ml, 25 mg/ml to about 150 mg/ml, 25 mg/ml to about 100 mg/ml, 50 mg/ml to about 200 mg/ml, 50 mg/ml to about 150 mg/ml, 50 mg/ml to about 100 mg/ml 100 mg/ml to about 200 mg/ml or 150 mg/ml to about 200 mg/ml anti-α4β7 integrin antibody.

The non-reducing sugar can be, but not limited to, mannitol, sorbital, sucrose, trehalose, raffinose, stachyose, melezitose, dextran, maltitol, lactitol, isomaltulose, palatinit and combinations thereof. In some embodiments, the ratio of the non-reducing sugar to the anti-α4β7 integrin antibody is at least 400:1 (mole:mole), at least 400:1 (mole:mole), at least 400:1 (mole:mole), at least 600:1 (mole:mole), at least 625:1 (mole:mole), at least 650:1 (mole:mole), at least 700:1 (mole:mole), at least 750:1 (mole:mole), at least 800:1 (mole:mole), at least 1000:1 (mole:mole), at least 1100:1 (mole:mole), at least 1200:1 (mole:mole), at least 1300:1 (mole:mole), at least 1400:1 (mole:mole), at least 1500:1 (mole:mole), at least 1600:1 (mole:mole), at least 1700:1 (mole:mole), at least 1800:1 (mole:mole), at least 1900:1 (mole:mole), or at least 2000:1 (mole:mole).

Exemplary formulations of the anti-α4β7 integrin antibody include, but are not limited, those described in, e.g., U.S. Patent Application Publication Nos. 2012/0282249, 2014/0377251; and 2014/0341885, the disclosures of which are herein incorporated by reference in their entirety for all purposes.

C. Methods of Administration of Combination Therapy

In another aspect, the present disclosure provides a combination therapy for the treatment of IBD, e.g., CD and UC. The combination therapy includes a therapeutically effective amount of a CCR9 inhibitor and a therapeutically effective amount of an anti-α4β7 integrin blocking antibody. The combination of therapeutic agents can act synergistically to effect the treatment or prevention of the various disorders. Using this approach, therapeutic efficacy can be achieved using lower dosages of each agent, thus reducing the potential for adverse side effects.

The term "therapeutically effective amount" means the amount of the subject compound that will elicit the biological or medical response of a cell, tissue, system, or animal, such as a human, that is being sought by the researcher, veterinarian, medical doctor or other treatment provider.

Depending on the disease status and the subject's condition, the compounds, antibodies, and formulations of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration. In addition, the compounds and antibodies may be formulated, alone or together, in suitable dosage unit formulations containing conventional nontoxic pharmaceutically acceptable carriers, adjuvants and vehicles appropriate for each rouse of administration. The present disclosure also contemplates administration of the compounds and antibodies of the present disclosure in a depot formulation.

In the treatment of IBD such as Crohn's disease and UC, an appropriate dosage level of a CCR9 inhibitor will generally be about 0.001 to 100 mg per kg patient body weight per day which can be administered in single or multiple doses. Preferably, the dosage level will be about 0.01 to about 50 mg/kg per day; more preferably about 0.05 to about 10 mg/kg per day. A suitable dosage level may be about 0.01 to 50 mg/kg per day, about 0.05 to 10 mg/kg per day, or about 0.1 to 5 mg/kg per day. Within this range the dosage may be 0.005 to 0.05 mg/kg per day, 0.05 to 0.5 mg/kg per day, 0.5 to 5.0 mg/kg per day, or 5.0 to 50 mg/kg per day.

For oral administration, the CCR9 inhibitor is preferably provided in the form of tablets containing 1.0 to 1000 milligrams of the active ingredient, particularly 1.0 mg, 5.0 mg, 10.0 mg, 15.0 mg, 20.0 mg, 25.0 mg, 50.0 mg, 75.0 mg, 100.0 mg, 150.0 mg, 200.0 mg, 250.0 mg, 300.0 mg, 400.0 mg, 500.0 mg, 600.0 mg, 750.0 mg, 800.0 mg, 900.0 mg, and 1000.0 mg of the active ingredient for the symptomatic adjustment of the dosage to the patient to be treated.

The CCR9 inhibitor may be administered on a regimen of 1 to 4 times per day, preferably once or twice per day.

In the treatment of IBD such as Crohn's disease and UC, an appropriate dosage level of an anti-α4β7 integrin antibody provides an effective amount of the antibody or a formulation thereof to induce remission of IBD in a human patient. In some embodiments, the therapeutically effective amount of anti-α4β7 integrin antibody is sufficient to achieve about 5 μg/ml to about 60 μg/ml mean trough serum concentration of anti-α4β7 integrin antibody at the end of the induction phase, e.g., about 5 μg/ml to about 60 μg/ml, about 10 μg/ml to about 50 μg/ml, about 15 μg/ml to about 45 μg/ml, about 20 μg/ml to about 30 μg/ml, about 25 μg/ml to about 35 μg/ml, or about 30 μg/ml to about 60 μg/ml mean trough serum concentration of anti-α4β7 integrin antibody at the end of the induction phase.

Suitable dosages of antibody can be administered from about 0.1 mg/kg, about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

In some embodiments, the total dose amount is about 6 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 650 mg, or more.

In some embodiment, the induction phase is for at least about 2 weeks, at least about 3 weeks, at least about 4 weeks, at least about 5 weeks, at least about 6 weeks, at least about 7 weeks, at least about 8 weeks, at least about 9 weeks, or at least about 10 weeks of treatment.

The treatment regime during the induction phase can include administration of a high dose, frequent administrations, or a combination of a high dose and frequent administrations of the anti-α4β7 integrin antibody or a formulation thereof. In some cases during the induction phase, a dose is administered once per day, every other day, every two days, every three days, once per week, every 10 days, once every two weeks, once every three weeks or once a month.

In some embodiments, the induction dosing is provided once at initiation of treatment (day 0) and once at about two weeks after initiation of treatment. The induction phase duration can be six weeks. In other embodiments, the induction phase duration is six weeks and a plurality of induction doses are administered during the first two weeks. In instances, when the human patient has severe IBD or is not responding to anti-TNFα therapy, the induction phase has longer duration than a patient who has mild to moderate IBD.

Also, in the treatment of IBD, an appropriate dosage level of an anti-α47β integrin antibody provides an effective amount of the antibody or a formulation thereof to maintain remission of IBD in a human patient. As such, during the maintenance phase of the treatment, the therapeutically effective amount of anti-α4β7 integrin antibody is sufficient to achieve about 1 μg/ml to about 25 μg/ml mean steady state trough serum concentration of anti-α4β7 integrin antibody during the maintenance phase, e.g., about 1 μg/ml to about 25 μg/ml, about 1 μg/ml to about 20 μg/ml, about 1 μg/ml to about 15 μg/ml, about 1 μg/ml to about 10 μg/ml, about 1

μg/ml to about 5 μg/ml, about 5 μg/ml to about 25 μg/ml, about 5 μg/ml to about 20 μg/ml, about 5 μg/ml to about 15 μg/ml, about 5 μg/ml to about 10 μg/ml, about 15 μg/ml to about 25 μg/ml, about 15 μg/ml to about 20 μg/ml, about 10 μg/ml to about 25 μg/ml, about 10 μg/ml to about 20 μg/ml, about 10 μg/ml to about 15 μg/ml, or about 20 μg/ml to about 25 μg/ml mean steady state trough serum concentration of anti-α4β7 integrin antibody at the end of the induction phase.

The maintenance dose can be administered once a week, once every other week, once every three weeks, once every 4 weeks, once every 5 weeks, once every 6 weeks, once every 7 weeks, once every 8 weeks, once every 9 weeks, or once every 10 weeks. In some embodiments during the maintenance phase, the same dosing amount is administered. In other embodiments during the maintenance phase, one or more different dosing amounts are administered over the maintenance phase. Additionally, depending on the disease course, the dosing frequency can be increased.

The anti-α4β7 integrin antibody or formulation thereof can be administered by injection, e.g., intravenous injection, intramuscular injection, subcutaneous injection, intraarterial injection, intraperitoneal injection, intravitreal injection, and the like. If the formulation is in a solid or lyophilized form, the process of administering the antibody can include reconstituting the dry formulation into a liquid formulation. In some embodiments, the antibody or formulation thereof can be administered topically, e.g., in a patch, cream, aerosol or suppository. In other embodiments, the topical routes of administration include nasal, inhalational or transdermal administration.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

The weight ratio of the CCR9 inhibitor described herein to the anti-α4β7 integrin antibody of the present disclosure may be varied and will depend upon the effective dose of each ingredient. Generally, an effective dose of each will be used. Thus, for example, wherein a CCR9 inhibitor is combined with an anti-α4β7 integrin antibody, the weight ratio of the CCR9 inhibitor to the anti-α4β7 integrin antibody will generally range from about 1000:1 to about 1:1000, preferably about 200:1 to about 1:200.

Combination therapy includes co-administration of the CCR9 inhibitor and the anti-α4β7 integrin antibody, sequential administration of the CCR9 inhibitor and the anti-α4β7 integrin antibody, administration of a composition containing the CCR9 inhibitor and the anti-α4β7 integrin antibody, or simultaneous administration of separate compositions such that one composition contains the CCR9 inhibitor and another composition contains the anti-α4β7 integrin antibody.

Co-administration includes administering the CCR9 inhibitor of the present invention within 0.5, 1, 2, 4, 6, 8, 10, 12, 16, 20, or 24 hours of the anti-α4β7 integrin antibody of the present invention. Co-administration also includes administering simultaneously, approximately simultaneously (e.g., within about 1, 5, 10, 15, 20, or 30 minutes of each other), or sequentially in any order. Moreover, the CCR9 inhibitor and anti-α4β7 integrin antibody can each be administered once a day, or two, three, or more times per day so as to provide the preferred dosage level per day.

The combination therapy can be administered at an induction phase or maintenance phase of the treatment regimen. In the induction phase, the combination therapy can be administered at an effective amount to induce immune tolerance to the antibody of the therapy, induce a clinical response, and/or ameliorate one or more symptoms of IBD. Also, if during the maintenance phase, there is a return of one or more symptoms of IBD or if there is a relapse from remission of the disease, a patient can be administered an amount corresponding to an induction phase treatment. During the maintenance phase, the combination therapy can be administered at an effective amount to continue the response achieve during the induction therapy and/or prevent the return of symptoms or relapse of IBD.

In some embodiments, one or more additional active ingredients such as an anti-inflammatory compound, e.g., sulfasalazine, azathioprine, 6-mercaptopurine, 5-aminosalicylic acid containing anti-inflammatories, a non-steroidal anti-inflammatory compound, and a steroidal anti-inflammatory compound; antibiotics commonly administered for control of IBD, e.g., ciprofloxacin and metronidazole; or another biologic agent, e.g., a TNFα antagonist can be administered in conjunction with the combination therapy disclosed herein.

D. Kits

In some aspects, provided herein are kits containing a CCR9 inhibitor and an anti-α4β7 integrin antibody disclosed herein that are useful for treating a disease or disorder characterized by inflammation of the gastrointestinal tract such as IBD, including CD, UC and indeterminate colitis. A kit can contain a pharmaceutical composition containing a CCR9 inhibitor compounds, e.g., a small molecule inhibitor of CCR9 and a pharmaceutical composition containing an anti-α4β7 integrin antibody. In some embodiments, the CCR9 inhibitor compound is vercirnon (Traficet-EN™) or CCX507. In some embodiments, the anti-α4β7 integrin antibody is vedolizumab. In some instances, the kit includes written materials e.g., instructions for use of the compound, antibody or pharmaceutical compositions thereof. Without limitation, the kit may include buffers, diluents, filters, needles, syringes, and package inserts with instructions for performing any methods disclosed herein.

IV. Examples

The following examples are offered to illustrate, but not to limit, the claimed invention.

Example 1: Using Combination Therapy of a CCR9 Inhibitor and an Anti-α4β7 Integrin Antibody to Treat Inflammatory Bowel Disease

A. Introduction

Homing of circulating cells into various tissues is a highly coordinated process involving specific chemokine receptors and cellular adhesion molecules. Trafficking of cells into the gut requires chemokine receptor CCR9-mediated chemotaxis towards the chemokine known as CCL25. CCR9 activation by CCL25 also triggers high affinity binding of cell surface α4β7 integrin with MAdCAM-expressing intestinal microvascular endothelium resulting in firm arrest and diapedesis into gut tissues.

Analysis of human colonic biopsies obtained from patients with colonic Crohn's disease showed strong positive correlation between CCR9 gene expression and that of the genes for TNF-α, as well as α4 and β7 integrins. These results showed that the regulation of genes implicated in gut inflammation are highly associated and tightly regulated in the colon. Vedolizumab, a humanized antibody against α4β7 integrin, was recently approved to treat patients with moderate to severe ulcerative colitis and Crohn's disease. However, its effects in combination with an antagonist of the gut homing chemokine receptor CCR9 have not been explored.

B. Methods

Adhesion assays were performed as follows. Human lymphocytes were isolated from total PBMCs and activated with α-CD3ε/α-CD28 (1 μg/mL; R&D Systems) in the presence of 1 μM retinoic acid (Sigma) and 1 ng/mL human IL12 (R&D Systems). In vitro activated T cells were further expanded for 5 days in the presence of 1 μM retinoic acid (RA) and 1 ng/mL human IL12. The expanded cells were stained with an anti CCR9 APC conjugated antibody (Cat. No. 248621; R&D Systems) and a conjugated anti-α4β7 integrin antibody (Act-1). The stained cells were analyzed by flow cytometry. Expression of CCR9 and α4β7 integrin in the expanded T cells was depicted as a 2-parameter scatterplot in FIG. 1A.

In vitro activated T cells were added to 96-well plate coated overnight with 0.3 μg/mL MAdCAM-1-Fc fusion protein (R&D Systems) in the presence of the following conditions: DMSO only, 500 ng human CCL25 (hCCL25; a CCR9 ligand) only, 1 μM CCX507 (a CCR9 small molecule inhibitor) only, or 500 ng hCCL25 and 1 μM CCX507. Adherent cells were quantified using CyQUANT® Cell Proliferation Assays (Thermo Fisher). The results are provided in FIG. 1B. The data shows that CCX507 limits the binding of RA-differentiated human T cells to MAdCAM-1 which can bind α4β7 integrin and helps to direct lymphocyte trafficking.

In vivo pharmacodynamic assays were performed as follows. FIG. 2A depicts the adoptive T cell transfer model used in the experiment. A detailed description of the method is found in, e.g., Tubo et al., *PLOS One,* 2012, 7(11):e50498. Briefly, CD8$^+$T cells isolated from donor OT-I TCR transgenic mice (B6.CD45.2). Leukocytes were isolated from the spleen and lymph node. The isolated CD8$^+$T cells were adoptively transferred into wild-type mice (B6. CD45.1). $1\times10^6$-$1\times10^7$ nave CD8$^+$ T cells were injected intraperitoneally into the recipient mouse.

24 hours post-transfer, the recipient CD45.1 mice were orally challenged with cholera toxin alone or cholera toxin and ovalbumin. The cholera toxin challenged mice were used as a mouse model of intestinal inflammation. After 96 hours, leukocytes were isolated from the spleen, lymph nodes, small bowel, colon, blood and liver. The number of donor-derived CD8$^+$T cells in the small intestine was determined by flow cytometry 96 hours post-challenge. A detailed description of the method is found in, e.g., Tubo et al., *PLOS One,* 2012, 7(11):e50498.

Figure 2B:
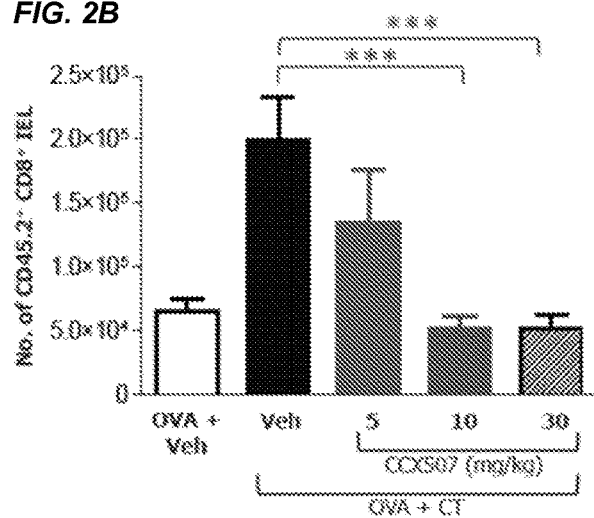
Figure 2C:
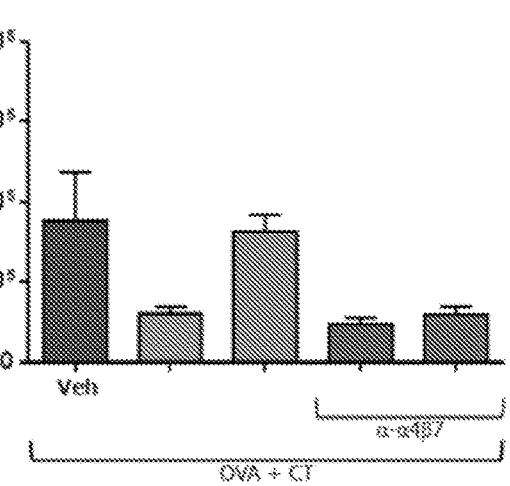

In addition, the cholera toxin challenged mice were administered with either 5-30 mg/kg of CCX507 or a dose of an anti-α4β7 integrin antibody. The number of donor-derived (OT-1 derived) CD8$^+$ intra-epithelial lymphocytes (IELs) were counted. The results are provided in FIG. 2B.

Figure 3:
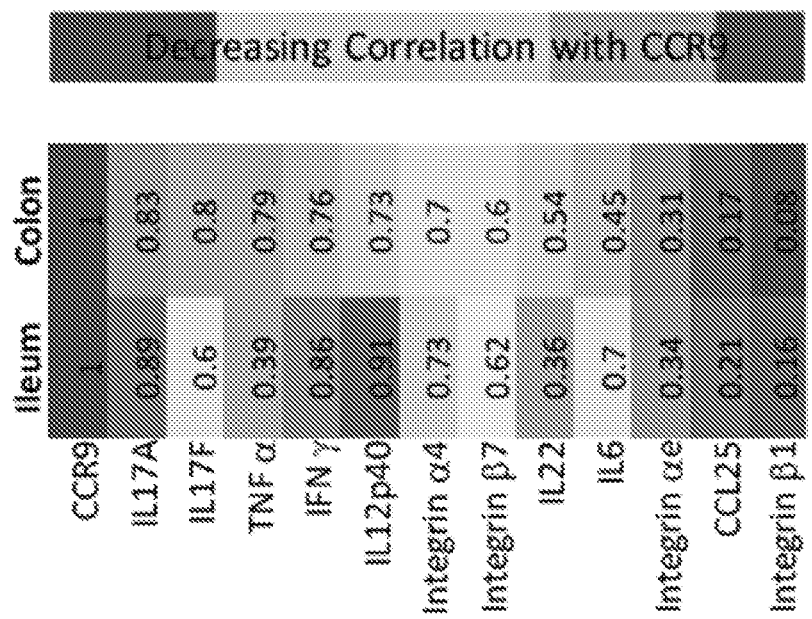
FIG. 3 shows an association of human CCR9 gene expression in the ileum and colon. Biopsy samples of patients with Crohn's disease were obtained. Normalized gene expression was derived from terminal ileum and colon samples.

QuantiGene® Plex assays (Affymetrix) were performed as follows. Matched ileum and colon biopsies from Crohn's disease patients were snap frozen in liquid nitrogen. Samples were homogenized according to manufacturer's protocols. Expression of genes was analyzed using a customized 37-plex panel (Affymetrix) and its expression was normalized to the housekeeping gene cyclophilin. FIG. 3 provides a comparison of expression levels of selected genes compared to the level of CCR9 expression.

Figure 4A:
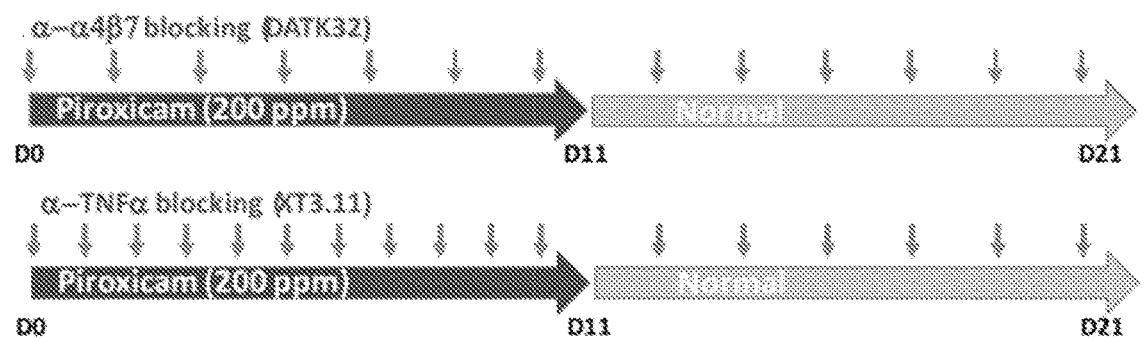
FIGS. 4A, 4B, 4C and 4D show that the combination of CCX507 and an anti-α4β7 integrin blocking antibody conferred greater protection against colitis compared to monotherapeutic regimens.

A mouse model of piroxicam accelerated colitis (chemically-induced colitis) was generated as follows. 7-week old Mdr1a$^{-/-}$ mice and an FVB control strain were provided with 200 ppm piroxicam (Sigma) mixed with powdered chow (food) in powdered diet feeding jars (Dyets, Inc.) for 10-12 days. Normal food was placed in wire bar lids for the duration of the experiment. Anti-α4β7 integrin blocking antibody (DATK32) was administered IP, q2d (via intraperitoneal injection every other day) at 100 μg per mouse. Anti-TNFα antibody (XT3.11) was administered IP, qd (via intraperitoneal injection every day) at 300 μg per mouse during the first 11 days when piroxicam was added to the powdered chow. Anti-TNFα antibody (XT3.11) was administered IP, q2d at 300 μg per mouse after piroxicam was removed. CCX507 (a CCR9 small molecule inhibitor) was administered SC, qd (via subcutaneous injection every day) at 30 mg/kg for the duration of the study. Mice in the study were observed and handled as approved by IACUC. FIG. 4A depicts the experimental design.

Figure 4B:
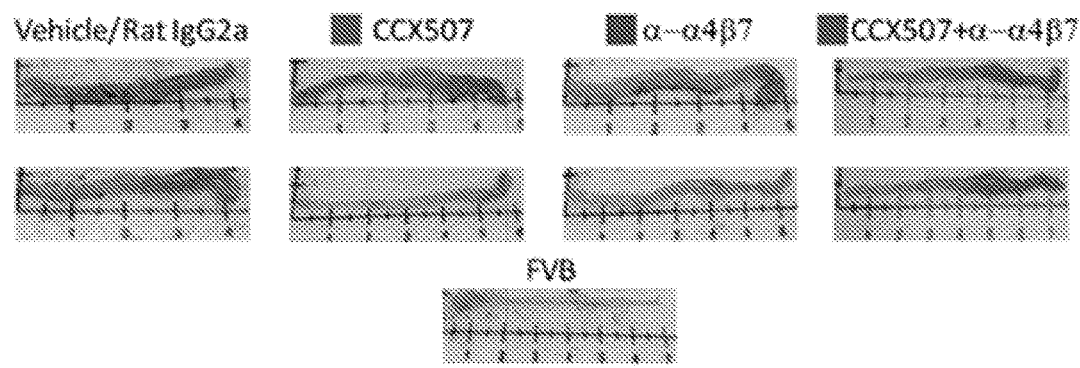
Figure 4C:
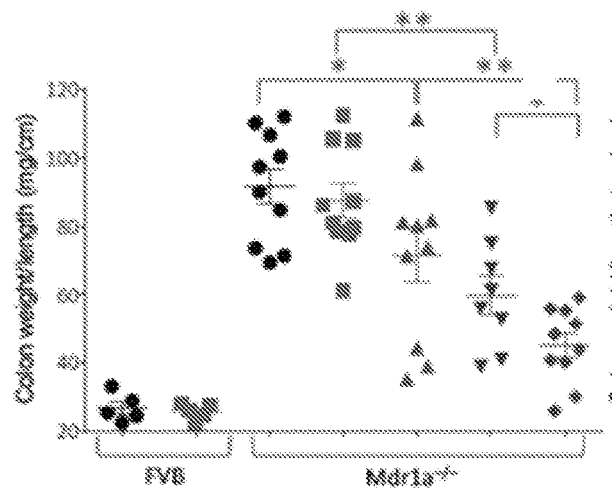
Figure 4D:
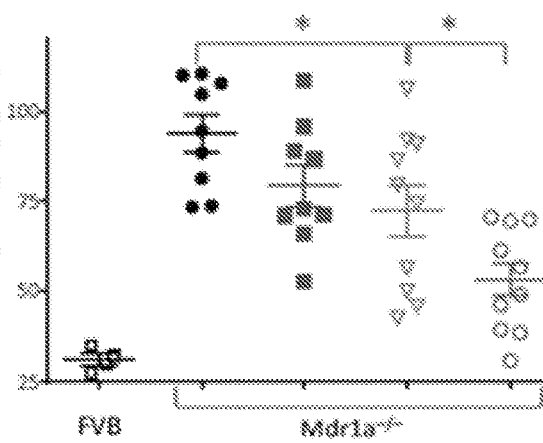

FIG. 4B shows representative images of the colon of mice receiving a vehicle control (1% HPMC) or a rat IgG2A isotype control, CCX507 (a CCR9 small inhibitor molecule) alone, an anti-α4β7 integrin blocking antibody alone, or CCX507 in addition to an anti-α4β7 integrin blocking antibody. Quantitative colon vs. weight ratios for the different treatment conditions is depicted in FIGS. 4C and 4D. The combination therapy of CCX507 and anti-α4β7 integrin blocking antibodies is shown in FIG. 4C. The combination therapy of CCX507 and anti-TNFα blocking antibodies is shown in FIG. 4D. Statistical analysis was performed using GraphPad Prism® (GraphPad Software) with the p-values represented in the following manner: *$p<0.05$; $p<0.01$; *$p<0.001$; ****$p<0.0001$.

Colon tissue, formalin fixed at the time of necropsy, was evaluated for histopathology by an independent, blinded pathologist. A total histological score was derived from the combined histological scores of Inflammation, glandular epithelial loss and erosion. These scores were based on the percentage of tissue affected in each section with a total of 6 sections cut per mouse.

Figure 5A:
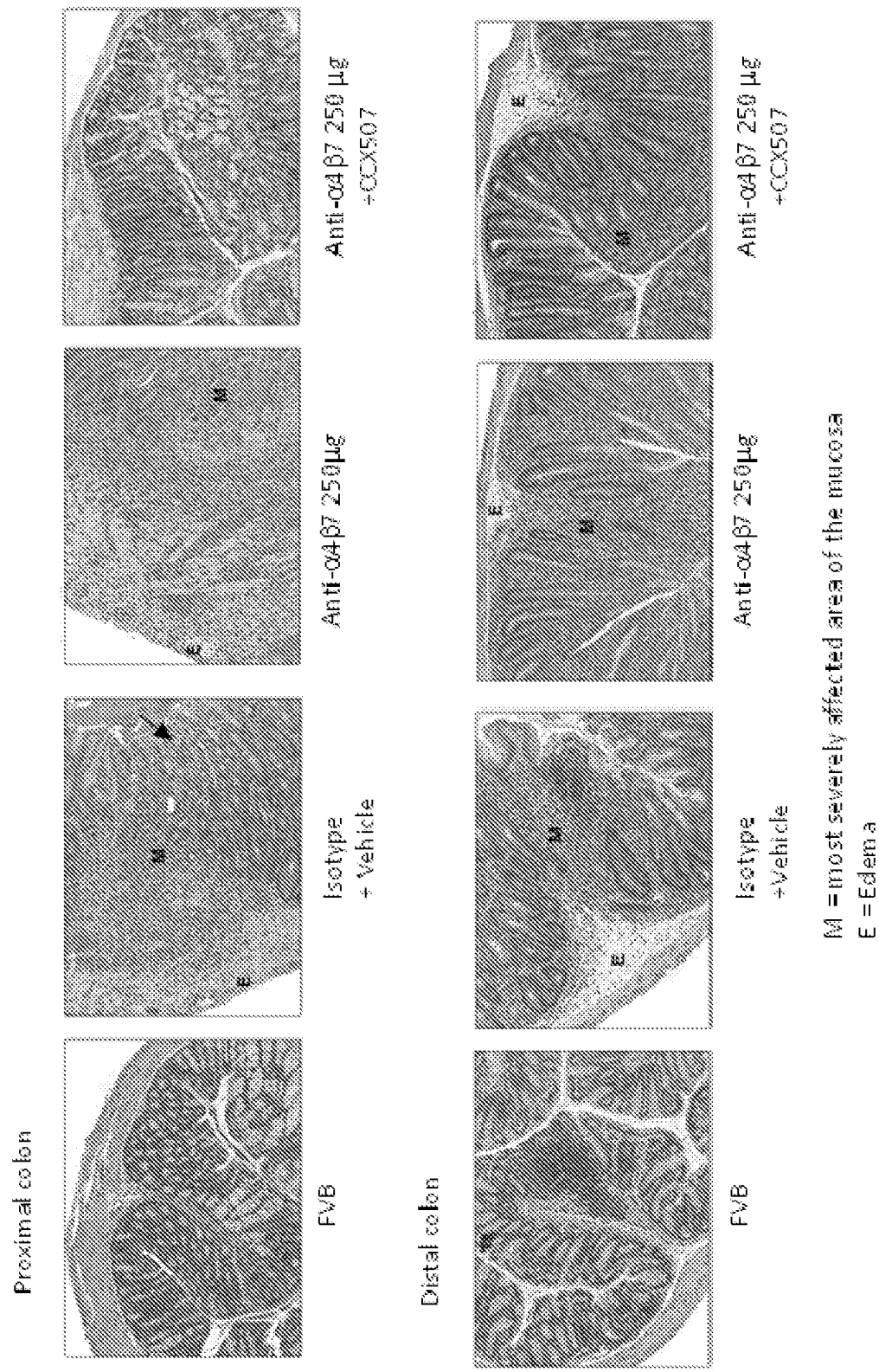
FIGS. 5A and 5B shows results from histological analysis of colon tissue from mice.

FIG. 5A shows representative images of both the proximal and distal colon from individual mice, representative of the mean histopathological score for each group. The combination of CCX507 in addition to anti-α4β7 antibody is shown in the right panel.

Figure 5B:
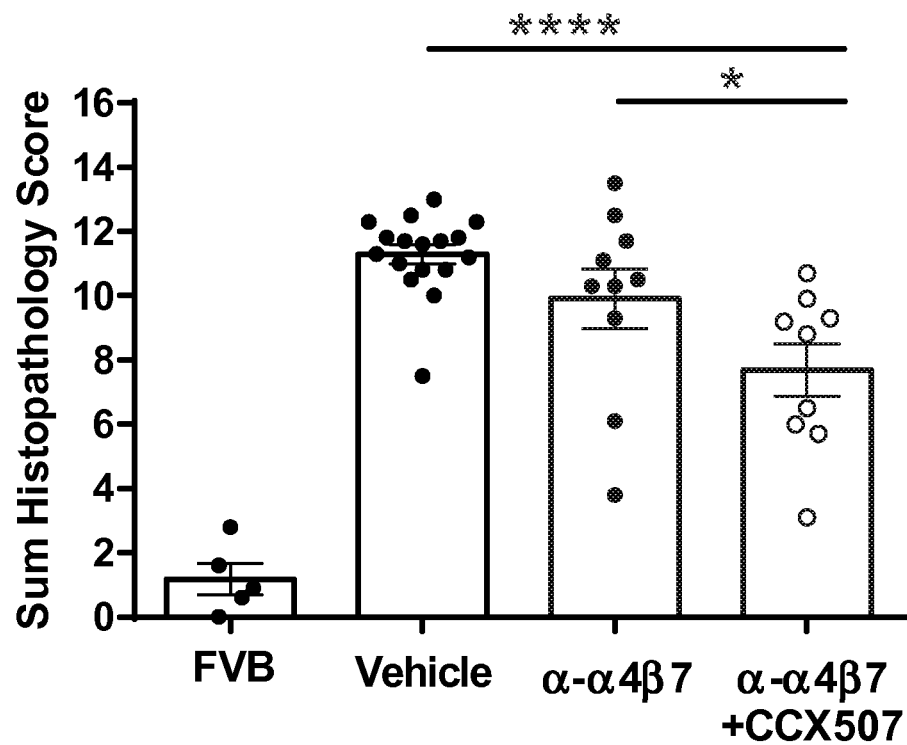

The sum histological score for all mice in the study is represented in FIG. 5B. Statistical analysis was performed by GraphPad Prism with the p-values represented as *$p<0.05$, ****$p<0.0001$.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating or reducing the development of inflammatory bowel disease in a mammal, comprising: administering a suitable amount of a CCR9 chemokine receptor inhibitor with an anti-α4β7 integrin blocking antibody, wherein the CCR9 chemokine receptor inhibitor is vercirnon, wherein the anti-α4β7 integrin blocking antibody is vedolizumab.

2. The method of claim 1, wherein the inflammatory bowel disease is Crohn's disease (CD) or ulcerative colitis (UC).

3. The method of claim 1, wherein the inflammatory bowel disease is Crohn's disease (CD).

4. The method of claim 1, wherein the inflammatory bowel disease is ulcerative colitis (UC).

5. The method of claim 1, wherein the CCR9 chemokine receptor inhibitor and the anti-α4β7 integrin blocking antibody are administered in a combination formulation.

6. The method of claim 1, wherein the CCR9 chemokine receptor inhibitor and the anti-α4β7 integrin blocking antibody are administered sequentially.

7. The method of claim 6, wherein the CCR9 chemokine receptor inhibitor is administered prior to or after the anti-α4β7 integrin blocking antibody.

8. The method of claim 6, wherein the CCR9 chemokine receptor inhibitor is administered after administration of the anti-α4β7 integrin blocking antibody.

9. The method of claim 1, further comprising administering one or more additional active ingredients selected from anti-inflammatory compounds and antibiotics.

10. The method of claim 1, wherein a weight ratio of the CCR9 inhibitor to the anti-α4β7 integrin antibody is from about 1000:1 to about 1:1000.

11. The method of claim 1, wherein the suitable amount of anti-α4β7 integrin antibody is from about 0.1 mg/kg, about 10 mg/kg.

12. The method of claim 1, wherein the suitable amount of anti-α4β7 integrin antibody is sufficient to achieve about 1 µg/ml to about 25 µg/ml mean steady state trough serum concentration of anti-α4β7 integrin antibody during a maintenance phase of treatment.

13. The method of claim 1, wherein the CCR9 inhibitor is administered once or twice per day.

14. The method of claim 1, wherein the CCR9 inhibitor is provided in the form of tablets containing 1.0 to 1000 milligrams of the CCR9 inhibitor.

15. The method of claim 1, wherein the suitable amount of CCR9 inhibitor is about 0.001 to 100 mg per kg patient body weight per day.

16. The method of claim 1, wherein the anti-α4β7 integrin antibody is a liquid formulation.

17. The method of claim 16, wherein the liquid formulation comprises the anti-α4β7 integrin antibody, a buffering agent, a non-reducing sugar, and a free amino acid.

18. The method of claim 17, wherein the liquid formulation further comprises an antioxidant or chelator.

* * * * *